(12) United States Patent
Hirata et al.

(10) Patent No.: US 10,040,997 B2
(45) Date of Patent: Aug. 7, 2018

(54) NEMATIC LIQUID CRYSTAL COMPOSITION AND LIQUID CRYSTAL DISPLAY ELEMENT INCLUDING SAME

(71) Applicant: DIC CORPORATION, Tokyo (JP)

(72) Inventors: Shinichi Hirata, Kitaadachi-gun (JP); Go Sudo, Kitaadachi-gun (JP); Shotaro Kawakami, Kitaadachi-gun (JP)

(73) Assignee: DIC CORPORATION, Tokyo (JP)

( * ) Notice: Subject to any disclaimer, the term of this patent is extended or adjusted under 35 U.S.C. 154(b) by 0 days.

(21) Appl. No.: 14/915,309

(22) PCT Filed: Sep. 4, 2014

(86) PCT No.: PCT/JP2014/073384
§ 371 (c)(1),
(2) Date: Feb. 29, 2016

(87) PCT Pub. No.: WO2015/034018
PCT Pub. Date: Mar. 12, 2015

(65) Prior Publication Data
US 2016/0215215 A1   Jul. 28, 2016

(30) Foreign Application Priority Data

Sep. 6, 2013  (JP) ................................ 2013-185016

(51) Int. Cl.
| | |
|---|---|
| *C09K 19/20* | (2006.01) |
| *C09K 19/32* | (2006.01) |
| *C09K 19/30* | (2006.01) |
| *C09K 19/44* | (2006.01) |
| *C07C 69/604* | (2006.01) |
| *C07C 69/753* | (2006.01) |
| *C07C 69/88* | (2006.01) |
| *C07D 213/79* | (2006.01) |
| *C07D 303/40* | (2006.01) |
| *C07D 305/06* | (2006.01) |
| *C09K 19/54* | (2006.01) |
| *C09K 19/04* | (2006.01) |
| *C09K 19/12* | (2006.01) |

(52) U.S. Cl.
CPC .......... *C09K 19/322* (2013.01); *C07C 69/604* (2013.01); *C07C 69/753* (2013.01); *C07C 69/88* (2013.01); *C07D 213/79* (2013.01); *C07D 303/40* (2013.01); *C07D 305/06* (2013.01); *C09K 19/20* (2013.01); *C09K 19/3066* (2013.01); *C09K 19/44* (2013.01); *C09K 19/542* (2013.01); *C07C 2601/14* (2017.05); *C09K 2019/0407* (2013.01); *C09K 2019/0448* (2013.01); *C09K 2019/122* (2013.01); *C09K 2019/3004* (2013.01); *C09K 2019/3009* (2013.01); *C09K 2019/548* (2013.01)

(58) Field of Classification Search
CPC ...................................................... C09K 19/20
See application file for complete search history.

(56) References Cited

U.S. PATENT DOCUMENTS

| | | | |
|---|---|---|---|
| 5,384,065 | A | 1/1995 | Geelhaar et al. |
| 6,066,268 | A | 5/2000 | Ichinose et al. |
| 9,102,869 | B2 | 8/2015 | Furusato |
| 2002/0014613 | A1 | 2/2002 | Klasen et al. |
| 2003/0222245 | A1 | 12/2003 | Klasen-Memmer et al. |
| 2004/0099842 | A1 | 5/2004 | Klasen-Memmer et al. |
| 2004/0146662 | A1 | 7/2004 | Klasen-Memmer et al. |
| 2005/0224758 | A1 | 10/2005 | Yamamoto et al. |
| 2006/0124896 | A1 | 6/2006 | Klasen-Memmer |
| 2006/0238696 | A1 | 10/2006 | Wen et al. |
| 2008/0149891 | A1 | 6/2008 | Klasen-Memmer |

(Continued)

FOREIGN PATENT DOCUMENTS

| | | |
|---|---|---|
| EP | 0 474 062 A2 | 3/1992 |
| JP | 8-104869 A | 4/1996 |

(Continued)

OTHER PUBLICATIONS

International Search Report dated Dec. 16, 2014, issued in counterpart International Application No. PCT/JP2014/073384 (2 pages).
International Search Report dated May 27, 2014, issued in International Application No. PCT/JP2014/055823 counterpart of U.S. Appl. No. 14/898,544 (2 pages).
Final Office Action dated Sep. 7, 2017, issued in U.S. Appl. No. 14/898,544.

(Continued)

*Primary Examiner* — Chanceity N Robinson
(74) *Attorney, Agent, or Firm* — Westerman, Hattori, Daniels & Adrian, LLP

(57) ABSTRACT

A nematic liquid crystal composition having negative dielectric anisotropy ($\Delta\varepsilon$), and a liquid crystal device element including the liquid crystal composition. The liquid crystal composition has sufficiently low viscosity ($\eta$), sufficiently low rotational viscosity ($\gamma1$), a large elastic constant ($K_{33}$), and a negative dielectric anisotropy ($\Delta\varepsilon$) whose absolute value is large, without reducing the refractive index anisotropy ($\Delta n$) or the nematic-isotropic liquid phase transition temperature ($T_{ni}$). A VA-mode liquid crystal display element including the liquid crystal composition, the liquid crystal display element having no or minimal display defects and having excellent display quality and a fast response. The liquid crystal display element including the liquid crystal composition is useful for an active matrix-addressed liquid crystal display element and used for, for example, a VA- or PSVA-mode liquid crystal display element.

13 Claims, No Drawings

(56) References Cited

U.S. PATENT DOCUMENTS

| | | |
|---|---|---|
| 2008/0191167 A1 | 8/2008 | Klasen-Memmer et al. |
| 2010/0025631 A1 | 2/2010 | Son et al. |
| 2010/0051864 A1 | 3/2010 | Klasen-Memmer |
| 2010/0149446 A1* | 6/2010 | Fujisawa ............ C09K 19/3852 349/38 |
| 2011/0043747 A1 | 2/2011 | Kawasaki |
| 2011/0149226 A1 | 6/2011 | Saito |
| 2011/0175027 A1 | 7/2011 | Hattori et al. |
| 2012/0162595 A1 | 6/2012 | Lee |
| 2012/0305843 A1 | 12/2012 | Klasen-Memmer |
| 2013/0038956 A1* | 2/2013 | Matsumoto ............ B60R 1/006 359/857 |
| 2013/0069002 A1* | 3/2013 | Yanai .................... C09K 19/42 252/299.61 |
| 2013/0265527 A1 | 10/2013 | Takeuchi et al. |
| 2014/0097383 A1 | 4/2014 | Furusato |
| 2015/0123032 A1 | 5/2015 | Sudo et al. |
| 2015/0218450 A1 | 8/2015 | Sudo et al. |

FOREIGN PATENT DOCUMENTS

| | | | |
|---|---|---|---|
| JP | 11-140447 A | | 5/1999 |
| JP | 2001-354967 A | | 12/2001 |
| JP | 2003-327965 A | | 11/2003 |
| JP | 2004-532344 A | | 10/2004 |
| JP | 2005-320511 A | | 11/2005 |
| JP | 2006-37054 A | | 2/2006 |
| JP | 2006-301643 A | | 11/2006 |
| JP | 2007-2132 A | | 1/2007 |
| JP | 2007002132 A | * | 1/2007 |
| JP | 2008-143902 A | | 6/2008 |
| JP | 2008-144135 A | | 6/2008 |
| JP | 2008-208365 A | | 9/2008 |
| JP | 2009-057562 A | | 3/2009 |
| JP | 2009270085 A | * | 11/2009 |
| JP | 2011-042696 A | | 3/2011 |
| JP | 2011-144274 A | | 7/2011 |
| JP | 2012-97222 A | | 5/2012 |
| JP | 2013-76061 A | | 4/2013 |
| WO | 2007/077872 A1 | | 7/2007 |
| WO | 2010/029843 A1 | | 3/2010 |
| WO | 2012/043386 A1 | | 4/2012 |
| WO | 2013/125379 A1 | | 8/2013 |
| WO | 2014/007118 A1 | | 1/2014 |

OTHER PUBLICATIONS

Non Final Office Action dated Apr. 9, 2018, issued in U.S. Appl. No. 14/898,544.

International Search Report dated Feb. 25, 2014, issued in application No. PCT/JP2014/050645 (corresponds to U.S. Appl. No. 14/422,275).

* cited by examiner

NEMATIC LIQUID CRYSTAL COMPOSITION AND LIQUID CRYSTAL DISPLAY ELEMENT INCLUDING SAME

TECHNICAL FIELD

The present invention relates to a nematic liquid crystal composition useful as a liquid crystal display material, the liquid crystal composition having negative dielectric anisotropy ($\Delta\varepsilon$), and to a liquid crystal device element including the liquid crystal composition.

BACKGROUND ART

Liquid crystal display devices have been used for, for example, clocks and watches, electronic calculators, various home electric appliances, measurement apparatuses, automotive panels, word processors, electronic notebooks, printers, computers, and television sets. Typical examples of a liquid crystal display mode include a twisted nematic (TN) mode, a super twisted nematic (STN) mode, a dynamic light scattering (DS) mode, a guest-host (GH) mode, an in-plane switching (IPS) mode, an optical compensated birefringence (OCB) mode, an electrically controlled birefringence (ECB) mode, a vertical alignment (VA) mode, a color super homeotropic (CSH) mode, and a ferroelectric liquid crystal (FLC) mode. Examples of a driving method include static driving, multiplex driving, a passive matrix method, and an active matrix (AM) method in which driving is performed with a thin-film transistor (TFT) or a thin-film diode (TFD).

Among these display modes, for example, the IPS mode, the ECB mode, the VA mode, or the CSH mode is characterized by using a liquid crystal material that has negative $\Delta\varepsilon$. Of these, in particular, the VA display mode driven by AM driving is used for applications, such as television sets, including display elements required to have high speeds and wide viewing angles.

Nematic liquid crystal compositions used for, for example, the VA display mode, are required to have low-voltage driving, a fast response, and a wide operating temperature range. That is, such liquid crystal compositions are each required to have negative $\Delta\varepsilon$ whose absolute value is large, low viscosity, and a high nematic-isotropic liquid phase transition temperature ($T_{ni}$). In view of the setting of $\Delta n \times d$, which is the product of refractive index anisotropy ($\Delta n$) and a cell gap (d), $\Delta n$ of a liquid crystal material needs to be adjusted within an appropriate range, depending on the cell gap. In addition, when a liquid crystal display element is used for, for example, a television set, emphasis is placed on a fast response. Thus, a liquid crystal material having low viscosity ($\eta$) is required.

Hitherto, various compounds each having negative $\Delta\varepsilon$ whose absolute value is large have been studied to improve the characteristics of liquid crystal compositions.

A liquid crystal composition containing compounds (A) and (B) with a 2,3-difluorophenylene skeleton described below (see Patent Literature 1) is disclosed as a liquid crystal material having negative $\Delta\varepsilon$.

[Chem. 1]

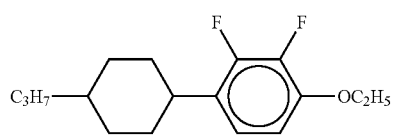

(A)

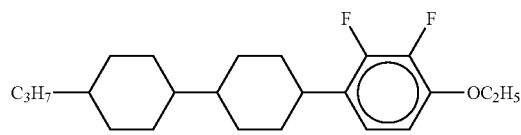

(B)

The liquid crystal composition contains compounds (C) and (D) serving as compounds having $\Delta\varepsilon$ of substantially zero. In the case of the liquid crystal composition, however, sufficiently low viscosity is not achieved for a liquid crystal composition for use in, for example, a liquid crystal television set required to have a fast response.

[Chem. 2]

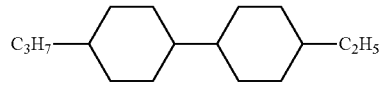

(C)

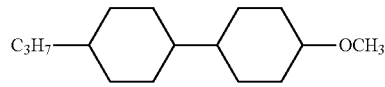

(D)

Liquid crystal compositions each containing a compound represented by formula (E) have already been disclosed and include a liquid crystal composition which contains compound (D) in combination with it and which has low $\Delta n$ (see Patent Literature 2); and a liquid crystal composition to which a compound (alkenyl compound), such as compound (F), containing an alkenyl group in its molecule is added to improve its response speed (see Patent Literature 3). To achieve both high $\Delta n$ and high reliability, further studies have been required.

[Chem. 3]

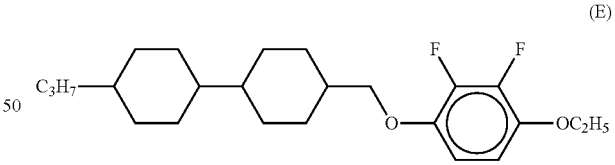

(E)

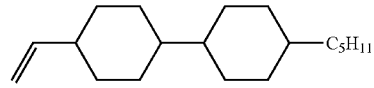

(F)

A liquid crystal composition containing a compound represented by formula (G) has already been disclosed (see Patent Document 4). This liquid crystal composition is also a liquid crystal composition that contains a compound containing an alkenyl compound, such as compound (F) described above. Thus, display defects, such as image persistence and display unevenness, are disadvantageously liable to occur.

[Chem. 4]

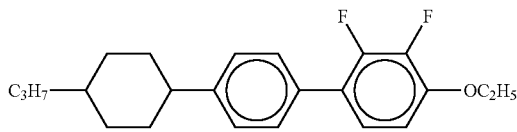

(G)

The influence of a liquid crystal composition containing an alkenyl compound on display defects has been already disclosed (see Patent Literature 5). However, in general, a reduction in alkenyl compound content increases η of the liquid crystal composition to cause difficulty in achieving a fast response. It is thus difficult to achieve both of the suppression of the display defects and the fast response.

As described above, it has been difficult to develop a liquid crystal composition which has negative Δε, which achieves both high Δn and low η, and which has no or minimal display defects only by the combinations of the compound having negative Δε with compounds (C), (D), and (F).

A liquid crystal composition in which formulae (A) and (G) are combined with formula (III-F31) having Δε of substantially zero is disclosed (see Patent Literature 6). However, in a production process of a liquid crystal display element, a compound with a low vapor pressure is vaporized at an extremely low pressure during the injection of a liquid crystal composition into a liquid crystal cell, so it was seemingly impossible to increase the content of the compound. Thus, in the liquid crystal composition, the content of formula (III-F31) is limited. Although the liquid crystal composition has Δn, the liquid crystal composition disadvantageously has significantly high viscosity.

[Chem. 5]

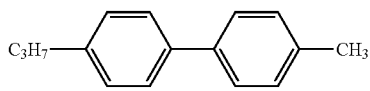

(III-F31)

In Patent Literatures 6 and 7, liquid crystal compositions containing compounds having fluorine-substituted terphenyl structures have already been disclosed.

Patent Literature 8 discloses that the use of a liquid crystal material having a large index (FoM) represented by (expression 1) improves the response speed of a homeotropic liquid crystal cell. However, the improvement in the response speed of the liquid crystal composition described in the specification is not sufficient.

[Math. 1]

$$FoM = K_{33} \cdot \Delta n^2 / \gamma 1$$ (expression 1)

$K_{33}$: elastic constant
$\Delta n$: refractive index anisotropy
$\gamma 1$: rotational viscosity Thus, a liquid crystal composition used for, for example, liquid crystal television sets required to have a fast response has been required to have a sufficiently low solid-nematic phase transition temperature ($T_{cn}$), sufficiently low viscosity (η), sufficiently low rotational viscosity (γ1), and a large elastic constant ($K_{33}$) without reducing the refractive index anisotropy (Δn) or the nematic-isotropic liquid phase transition temperature ($T_{ni}$).

CITATION LIST

Patent Literature

PTL 1: Japanese Unexamined Patent Application Publication No. 8-104869
PTL 2: European Patent Application Publication No. 0474062
PTL 3: Japanese Unexamined Patent Application Publication No. 2006-37054
PTL 4: Japanese Unexamined Patent Application Publication No. 2001-354967
PTL 5: Japanese Unexamined Patent Application Publication No. 2008-144135
PTL 6: International Publication No. 2007/077872
PTL 7: Japanese Unexamined Patent Application Publication No. 2003-327965
PTL 8: Japanese Unexamined Patent Application Publication No. 2006-301643

SUMMARY OF INVENTION

Technical Problem

It is an object of the present invention to provide a liquid crystal composition having a sufficiently low solid-nematic phase transition temperature ($T_{cn}$), sufficiently low viscosity (η), sufficiently low rotational viscosity (γ1), a large elastic constant ($K_{33}$), and negative dielectric anisotropy (Δε) whose absolute value is large, without reducing the refractive index anisotropy (Δn) or the nematic-isotropic liquid phase transition temperature ($T_{ni}$), and to provide, for example, a VA-mode liquid crystal display element including the liquid crystal composition, the liquid crystal display element having no or minimal display defects and having excellent display quality and a fast response.

Solution to Problem

The inventors have conducted studies on various compounds having difluorobenzene skeletons and have found that the foregoing problems are solved by a specific combination of compounds. This finding has led to the completion of the present invention.

In the present invention, provided is a liquid crystal composition containing one or two or more compounds represented by general formula (I):

[Chem. 6]

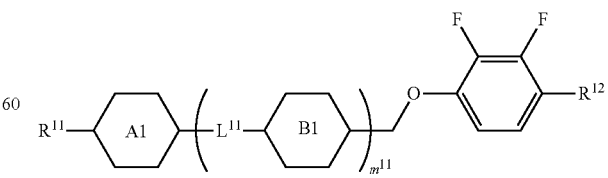

(I)

(wherein in the formula, $R^{11}$ and $R^{12}$ each represent an alkyl group having 1 to 8 carbon atoms or an alkenyl group having 2 to 8 carbon atoms, —$CH_2$— or nonadjacent two or more —CH$_2$—'s in the group may be independently replaced with —O— or —S—, one or two or more hydrogen atoms present in the group may be independently replaced with a fluorine atom or a chlorine atom, L$^{11}$ represents —OCH$_2$—, —CH$_2$O—, —CF$_2$O—, —OCF$_2$—, —CH$_2$CH$_2$—, —CF$_2$CF$_2$—, or a single bond, when a plurality of L$^{11}$'s are present, they may be the same or different, m$^{11}$ represents 0, 1, or 2, ring A1 represents a 1,4-phenylene group, ring B1 independently represents a trans-1,4-cyclohexylene group, a 1,4-phenylene group, a 2-fluoro-1,4-phenylene group, a 3-fluoro-1,4-phenylene group, a 3,5-difluoro-1,4-phenylene group, a 2,3-difluoro-1,4-phenylene group, a 1,4-cyclohexenylene group, a 1,4-bicyclo[2.2.2]octylene group, a piperidine-1,4-diyl group, a naphthalene-2,6-diyl, a decahydronaphthalene-2,6-diyl group, or a 1,2,3,4-tetrahydronaphthalene-2,6-diyl group, when a plurality of rings B1 are present, they may be the same or different, and ring B1 may be substituted with an alkyl group having 1 to 12 carbon atoms, a halogenated alkyl group having 1 to 12 carbon atoms, an alkoxy group having 1 to 12 carbon atoms, a halogenated alkoxy group having 1 to 12 carbon atoms, a halogen, a cyano group, or a nitro group). Furthermore, a liquid crystal display element including the liquid crystal composition is provided.

Advantageous Effects of Invention

A liquid crystal composition of the present invention has a sufficiently low solid-nematic phase transition temperature (T$_{cn}$), sufficiently low viscosity (μ), sufficiently low rotational viscosity (γ1), a large elastic constant (K$_{33}$), a high voltage holding ratio (VHR), and negative dielectric anisotropy (Δε) whose absolute value is large, without reducing the refractive index anisotropy (Δn) or the nematic-isotropic liquid phase transition temperature (T$_{ni}$). Thus, for example, a VA- or PSA-mode liquid crystal display element including the liquid crystal composition has no or minimal display defects and has excellent display quality and a fast response. The liquid crystal composition of the present invention is particularly effective for a liquid crystal display element including a cell with small thickness, the liquid crystal display element being required to have high Δn.

DESCRIPTION OF EMBODIMENTS

A liquid crystal composition of the present invention contains a compound represented by formula (I):

[Chem. 7]

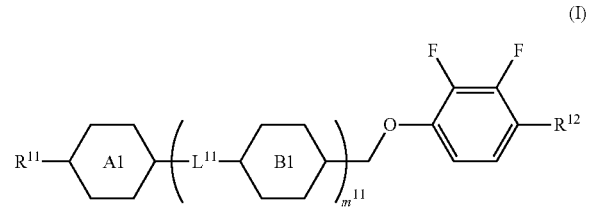

(I)

In the formula, R$^{11}$ and R$^{12}$ each represent an alkyl group having 1 to 8 carbon atoms or an alkenyl group having 2 to 8 carbon atoms. —CH$_2$— or nonadjacent two or more —CH$_2$—'s in the group may be independently replaced with —O— or —S—. One or two or more hydrogen atoms present in the group may be independently replaced with a fluorine atom or a chlorine atom. R$^{11}$ preferably represents an alkyl group having 1 to 8 carbon atoms, an alkoxy group having 1 to 8 carbon atoms, or an alkenyl group having 2 to 8 carbon atoms, and more preferably represents an alkyl group having 1 to 5 carbon atoms or an alkenyl group having 2 to 5 carbon atoms. R$^{12}$ preferably represents an alkyl group having 1 to 8 carbon atoms, an alkoxy group having 1 to 8 carbon atoms, an alkenyl group having 2 to 8 carbon atoms, or an alkenyloxy group having 2 to 8 carbon atoms, more preferably an alkyl group having 1 to 5 carbon atoms, an alkoxy group having 1 to 5 carbon atoms, or an alkenyloxy group having 2 to 5 carbon atoms, and even more preferably an alkoxy group having 1 to 5 carbon atoms or an alkenyloxy group having 2 to 5 carbon atoms.

When R$^{11}$ and R$^{12}$ each represent an alkenyl group, the alkenyl group is preferably a substituent represented by formulae (Alkenyl-1) to (Alkenyl-4):

[Chem. 8]

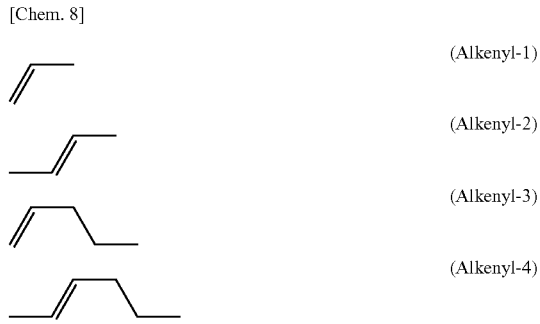

(wherein in the formulae, the right end of each of the groups is bonded to the ring structure). L$^{11}$ represents —OCH$_2$—, —CH$_2$O—, —CF$_2$O—, —OCF$_2$—, —CH$_2$CH$_2$—, —CF$_2$CF$_2$—, or a single bond, preferably —CH$_2$CH$_2$— or a single bond, and more preferably a single bond.

When a plurality of L$^{11}$'s are present, they may be the same or different.

m$^{11}$ represents 0, 1, or 2, and preferably 0 or 1.

Ring A1 represents a 1,4-phenylene group. Ring B1 represents a trans-1,4-cyclohexylene group, a 1,4-phenylene group, 2-fluoro-1,4-phenylene group, a 3-fluoro-1,4-phenylene group, a 3,5-difluoro-1,4-phenylene group, a 2,3-difluoro-1,4-phenylene group, a 1,4-cyclohexenylene group, a 1,4-bicyclo[2.2.2]octylene group, a piperidine-1,4-diyl group, a naphthalene-2,6-diyl group, a decahydronaphthalene-2,6-diyl group, or a 1,2,3,4-tetrahydronaphthalene-2,6-diyl group, preferably a trans-1,4-cyclohexylene group, a 1,4-phenylene group, a 2-fluoro-1,4-phenylene group, a 3-fluoro-1,4-phenylene group, or a 2,3-difluoro-1,4-phenylene group, more preferably a trans-1,4-cyclohexylene group, a 1,4-phenylene group, a 2-fluoro-1,4-phenylene group, or a 3-fluoro-1,4-phenylene group, and even more preferably a trans-1,4-cyclohexylene group or a 1,4-phenylene group.

When a plurality of rings B1 are present, they may be the same or different.

Ring B1 may be unsubstituted or substituted with an alkyl group having 1 to 12 carbon atoms, a halogenated alkyl group having 1 to 12 carbon atoms, an alkoxy group having 1 to 12 carbon atoms, a halogenated alkoxy group having 1 to 12 carbon atoms, a halogen, a cyano group, or a nitro group, preferably unsubstituted or substituted with an alkyl group having 1 to 12 carbon atoms, a halogenated alkyl group having 1 to 12 carbon atoms, an alkoxy group having 1 to 12 carbon atoms, a halogenated alkoxy group having 1 to 12 carbon atoms, or a halogen, more preferably unsubstituted or substituted with an alkyl group having 1 to 12 carbon atoms, a halogenated alkyl group having 1 to 12 carbon atoms, or a halogen, and even more preferably unsubstituted or substituted with a halogen.

In the present invention, one or two or more of the compounds represented by formula (I) are preferably contained. The content of the compounds is 1% to 100% by mass, preferably 2% to 80% by mass, more preferably 3% to 50% by mass, and particularly preferably 3% to 30% by mass.

In the case where emphasis is placed on a reduction in the viscosity of the liquid crystal composition, among the compounds represented by formula (I), it is preferable to increase the content of a compound whose $R^{11}$ or $R^{12}$ represents an alkenyl group or an alkenyloxy group. The lower limit is preferably 2% by mass, more preferably 5% by mass, still more preferably 10% by mass, still even more preferably 15% by mass. In the case where emphasis is placed on the stability of the liquid crystal composition against ultraviolet rays, among the compounds represented by formula (I), it is preferable to reduce the content of a compound whose $R^{11}$ or $R^{12}$ represents an alkenyl group or an alkenyloxy group. The upper limit is preferably 15% by mass, more preferably 10% by mass, and still more preferably 5% by mass.

Examples of the compounds represented by general formula (I) include compounds represented by general formulae (I-A), (I-B), (I-C), (I-D), (I-E), (I-F), and (I-G). The compounds represented by general formulae (I-A), (I-B), and (I-C) are preferred. The compounds represented by general formulae (I-B) and (I-C) are more preferred. The compounds represented by general formula (I-B) are still more preferred.

[Chem. 9]

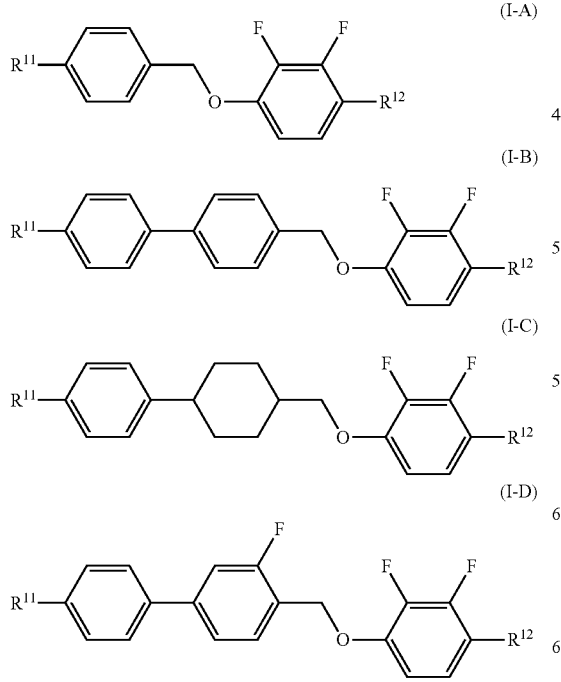

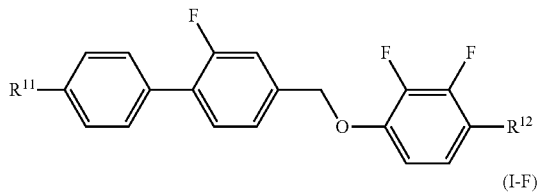

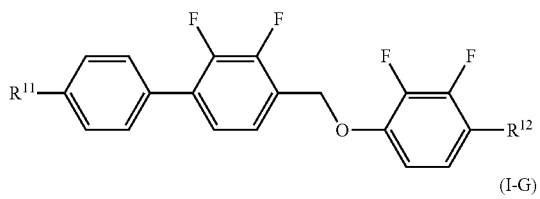

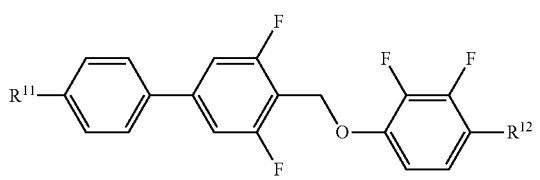

In the formulae, $R^{11}$ and $R^{12}$ are as defined above.

The liquid crystal composition of the present invention preferably contains, as a nonpolar compound having a dielectric anisotropy (Δε) of about zero, a compound selected from the group consisting of compounds represented by general formulae (IV-1) to (IV-3). One or two or more compounds selected from the group consisting of the compounds represented by general formulae (IV-1) to (IV-3) are preferably contained. One to ten compounds selected therefrom are more preferred. One to five compounds selected therefrom are still more preferred. The total content thereof is preferably 5% to 70% by mass, more preferably 5% to 50% by mass, and particularly preferably 5% to 40% by mass.

[Chem. 10]

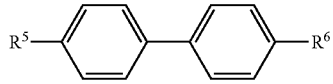

In each of the formulae, $R^5$ represents an alkyl group having 1 to 5 carbon atoms or an alkenyl group having 2 to 5 carbon atoms. $R^6$ represents an alkyl group having 1 to 5 carbon atoms, an alkoxyl group having 1 to 5 carbon atoms, an alkenyl group having 2 to 5 carbon atoms, or an alkenyloxy group having 2 to 5 carbon atoms. One —CH$_2$— or nonadjacent two or more —CH$_2$—'s present in the group may be independently replaced with —O— or —S—. One or two or more hydrogen atoms present in the group may be independently replaced with a fluorine atom. $R^5$ preferably represents an alkyl group having 1 to 5 carbon atoms or an alkenyl group having 2 to 4 carbon atoms. $R^6$ preferably represents an alkyl group having 1 to 5 carbon atoms, an alkoxyl group having 1 to 3 carbon atoms, or an alkenyl group having 2 to 4 carbon atoms, and more preferably an alkyl group having 1 to 5 carbon atoms or an alkenyl group having 2 to 4 carbon atoms.

Among the group of the compounds represented by general formulae (IV-1) to (IV-3), a compound represented by general formula (IV-1) is particularly preferably contained. The content of the compound represented by general formula (IV-1) is preferably 5% to 50% by mass and more preferably 10% to 40% by mass.

In the liquid crystal composition of the present invention, the liquid crystal composition contains a substantially dielectrically neutral compound. Thus, other physical properties, such as the nematic-isotropic liquid phase transition temperature ($T_{ni}$), the temperature range of the liquid crystal phase, the viscosity ($\eta$) at the phase transition temperature, the rotational viscosity ($\gamma1$), and the refractive index anisotropy ($\Delta n$) may be controlled to preferred ranges without affecting $\Delta\varepsilon$. Examples of such a compound that is preferably contained include compounds represented by general formula (N3):

[Chem. 11]

(N3)

$R^p$ and $R^q$ each independently represent an alkyl group having 1 to 10 carbon atoms or an alkenyl group having 2 to 10 carbon atoms. One —$CH_2$— or two or more nonadjacent —$CH_2$—'s present in the group may be independently replaced with —O— or —S—. One or two or more hydrogen atoms present in the group may be replaced with a fluorine atom or a chlorine atom. $R^p$ and $R^q$ each independently preferably represent an alkyl group having 1 to 8 carbon atoms, an alkoxy group having 1 to 8 carbon atoms, an alkenyl group having 2 to 8 carbon atoms, or an alkenyloxy group having 2 to 8 carbon atoms, more preferably an alkyl group having 1 to 5 carbon atoms, an alkoxy group having 1 to 5 carbon atoms, an alkenyl group having 2 to 5 carbon atoms, or an alkenyloxy group having 3 to 6 carbon atoms, and particularly preferably an alkyl group having 1 to 5 carbon atoms, an alkoxy group having 1 to 5 carbon atoms, or an alkenyl group having 2 to 4 carbon atoms. Preferably, $R^p$ and $R^q$ each have a linear structure. When $R^p$ and $R^q$ each represent an alkenyl group, the alkenyl group preferably has a structure represented by one of formulae (Alkenyl-1) to (Alkenyl-4):

[Chem. 12]

(Alkenyl-1)

(Alkenyl-2)

(Alkenyl-3)

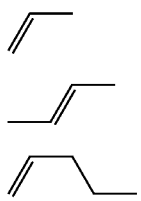

(Alkenyl-4)

(wherein in the formulae, the right end of each of the groups is bonded to the ring structure).

Ring J, ring F, and ring K each independently represent a trans-1,4-cyclohexylene group, a 1,4-phenylene group, a 2-fluoro-1,4-phenylene group, a 3-fluoro-1,4-phenylene group, a 3,5-difluoro-1,4-phenylene group, a 1,4-cyclohexenylene group, a 1,4-bicyclo[2.2.2]octylene group, a piperidine-1,4-diyl group, a naphthalene-2,6-diyl group, a decahydronaphthalene-2,6-diyl group, or a 1,2,3,4-tetrahydronaphthalene-2,6-diyl group, preferably a trans-1,4-cyclohexylene group, a 1,4-phenylene group, a 3-fluoro-1,4-phenylene group, a 3,5-difluoro-1,4-phenylene group, a 1,4-cyclohexenylene group, a 1,4-bicyclo[2.2.2]octylene group, a piperidine-1,4-diyl group, a naphthalene-2,6-diyl group, a decahydronaphthalene-2,6-diyl group, or a 1,2,3,4-tetrahydronaphthalene-2,6-diyl group, more preferably a trans-1,4-cyclohexylene group, a 1,4-phenylene group, a 3-fluoro-1,4-phenylene group, or a 1,4-bicyclo[2.2.2]octylene group, and particularly preferably a trans-1,4-cyclohexylene group or a 1,4-phenylene group.

$Z^{11}$ and $Z^{12}$ each independently represent —$OCH_2$—, —$CH_2O$—, —$CF_2O$—, —$OCF_2$—, —$CH_2CH_2$—, —$CF_2CF_2$—, or a single bond, preferably —$CH_2O$—, —$CF_2O$—, or a single bond, and more preferably —$CH_2O$— or a single bond.

Specifically, regarding a specific structure of general formula (N3), compounds represented by general formulae (N3-1) to (N3-9) are preferred.

[Chem. 13]

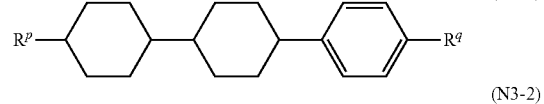

(N3-1)

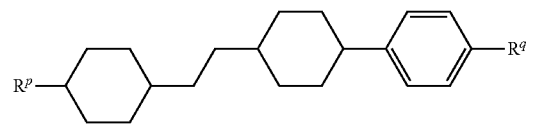

(N3-2)

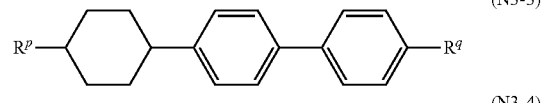

(N3-3)

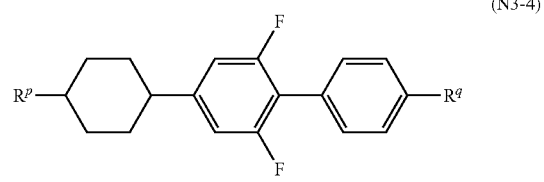

(N3-4)

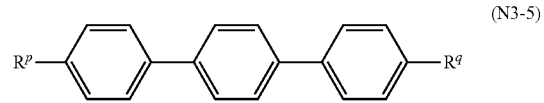

(N3-5)

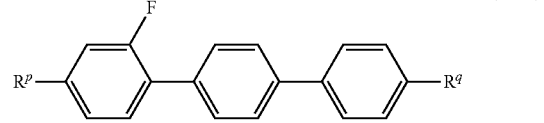

(N3-6)

-continued (N3-7)

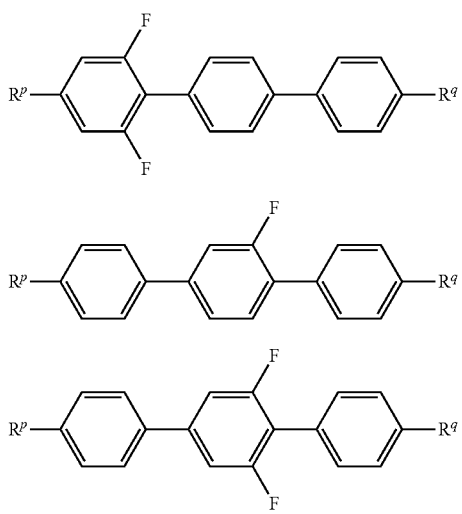

(N3-8)

(N3-9)

$R^p$ and $R^q$ are as defined above.

Among the compounds represented by general formulae (N3-1) to (N3-9), the compounds represented by general formulae (N3-1), (N3-3), (N3-4), (N3-5), (N3-8), or (N3-9) are preferred. The compounds represented by general formulae (N3-1), (N3-3), (N3-5), and (N3-8) are more preferred.

The liquid crystal composition of the present invention preferably contains 1 to 10 compounds and particularly preferably 2 to 8 compounds represented by general formula (N-3). The content of the compounds represented by general formula (N-3) is preferably 0% to 70% by mass, more preferably 0% to 60% by mass, and particularly preferably 5% to 50% by mass.

The liquid crystal composition of the present invention may contain a compound having negative Δε whose absolute value is more than 3. Specifically, compounds represented by general formula (II) are preferred. None of the compounds represented by formula (I) are included in the compounds represented by formula (II).

[Chem. 14]

(II)

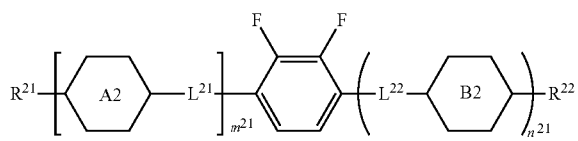

In the formula, $R^{21}$ and $R^{22}$ each represent an alkyl group having 1 to 8 carbon atoms or an alkenyl group having 2 to 8 carbon atoms. —CH$_2$— or nonadjacent two or more —CH$_2$—'s in the group may be independently replaced with —O— or —S—. One or two or more hydrogen atoms present in the group may be independently replaced with a fluorine atom or a chlorine atom. Each of $R^{21}$ and $R^{22}$ preferably has a linear structure and is preferably unsubstituted. More preferably, $R^{21}$ and $R^{22}$ each independently represent an alkyl group having 1 to 5 carbon atoms, an alkoxyl group having 1 to 5 carbon atoms, an alkenyl group having 2 to 5 carbon atoms, or an alkenyloxy group having 2 to 5 carbon atoms.

When $R^{21}$ and $R^{22}$ each represent an alkenyl group, the alkenyl group preferably has a structure represented by one of formulae (Alkenyl-1) to (Alkenyl-4):

[Chem. 15]

 (Alkenyl-1)

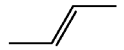 (Alkenyl-2)

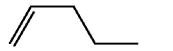 (Alkenyl-3)

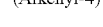 (Alkenyl-4)

(wherein in the formulae, the right end of each of the groups is bonded to the ring structure).

$L^{21}$ and $L^{22}$ each represent —OCH$_2$—, —CH$_2$O—, —CF$_2$O—, —OCF$_2$—, —CH$_2$CH$_2$—, —CF$_2$CF$_2$—, or a single bond, preferably —CH$_2$O—, —CF$_2$O—, or a single bond, and more preferably —CH$_2$O— or a single bond. When a plurality of $L^{11}$'s and a plurality of $L^{22}$'s are present, they may be the same or different.

$m^{21}$ and $n^{21}$ each independently represent 0, 1, or 2. $m^{21}+n^{21}$ represents 1, 2, or 3, and preferably 1 or 2.

Ring A2 and ring B2 each independently represent a trans-1,4-cyclohexylene group, a 1,4-phenylene group, a 2-fluoro-1,4-phenylene group, a 3-fluoro-1,4-phenylene group, a 3,5-difluoro-1,4-phenylene group, a 2,3-difluoro-1,4-phenylene group, a 1,4-cyclohexenylene group, a 1,4-bicyclo[2.2.2]octylene group, a piperidine-1,4-diyl group, a naphthalene-2,6-diyl group, a decahydronaphthalene-2,6-diyl group, or a 1,2,3,4-tetrahydronaphthalene-2,6-diyl group, and preferably a trans-1,4-cyclohexylene group, a 1,4-phenylene group, a 2-fluoro-1,4-phenylene group, a 3-fluoro-1,4-phenylene group, a 3,5-difluoro-1,4-phenylene group, or a 2,3-difluoro-1,4-phenylene group.

When a plurality of rings A2 and/or a plurality of rings B2 are present, they may be the same or different. Ring A2 and ring B2 may be each independently substituted with an alkyl group having 1 to 12 carbon atoms, a halogenated alkyl group having 1 to 12 carbon atoms, an alkoxy group having 1 to 12 carbon atoms, a halogenated alkoxy group having 1 to 12 carbon atoms, a halogen, a cyano group, or a nitro group, and preferably are each independently unsubstituted or substituted with an alkyl group having 1 to 12 carbon atoms, an alkoxy group having 1 to 12 carbon atoms, or a halogen.

As the compounds represented by general formula (II), specifically, compounds represented by general formulae (II-A1) to (II-A5) and (II-B1) to (II-B5) are preferred. Of these, the compounds represented by general formulae (II-A1) to (II-A5) are more preferred. The compounds represented by general formula (II-A1) or (II-A3) are particularly preferred.

[Chem. 16]

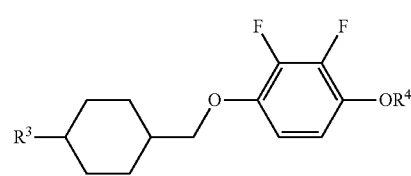
(II-A1)

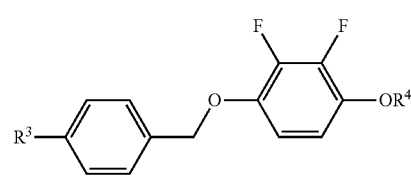
(II-A2)

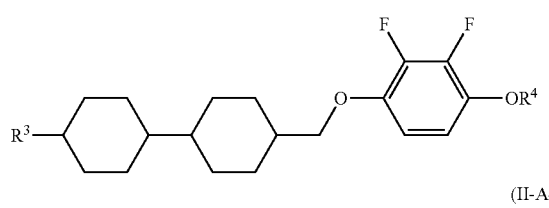
(II-A3)

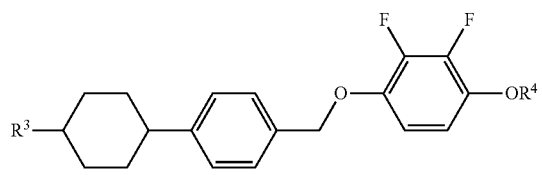
(II-A4)

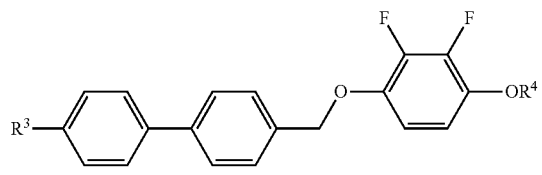
(II-A5)

[Chem. 17]

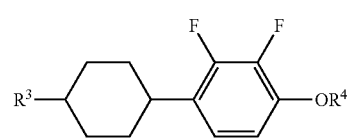
(II-B1)

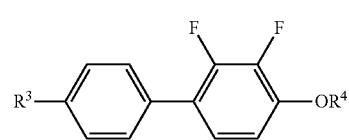
(II-B2)

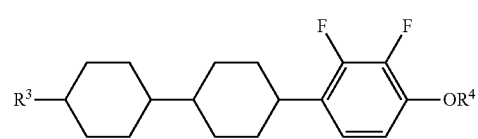
(II-B3)

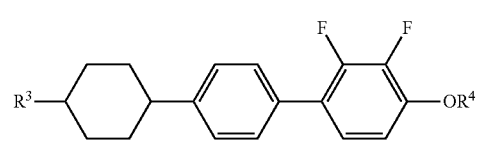
(II-B4)

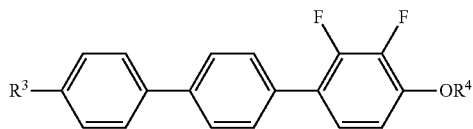
(II-B5)

In each of the formulae, $R^3$ and $R^4$ each independently represent an alkyl group having 1 to 5 carbon atoms, or an alkenyl group having 2 to 5 carbon atoms. One —CH$_2$— or two or more nonadjacent —CH$_2$—'s present in the group may be independently replaced with —O— or —S—. One or two or more hydrogen atoms present in the group may be independently replaced with a fluorine atom.

The compounds represented by general formula (II) are preferably compounds represented by general formula (V). In this case, one or two or more of the compounds represented by general formula (V) are preferably contained. The content thereof is preferably 2% to 30% by mass, more preferably 2% to 25% by mass, and particularly preferably 3% to 20% by mass.

[Chem. 18]

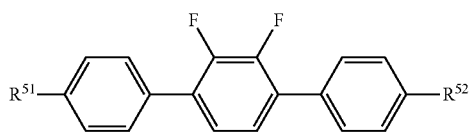
(V)

In the formula, $R^{51}$ and $R^{52}$ each independently represent an alkyl group having 1 to 8 carbon atoms, an alkoxyl group having 1 to 8 carbon atoms, an alkenyl group having 2 to 8 carbon atoms, or an alkenyloxy group having 2 to 8 carbon atoms. One —CH$_2$— or two or more nonadjacent —CH$_2$—'s present in the group may be independently replaced with —O— or —S—. One or two or more hydrogen atoms present in the group may be replaced with a fluorine atom. $R^{51}$ and $R^{52}$ each independently preferably represent an alkyl group having 1 to 5 carbon atoms or an alkenyl group having 2 to 5 carbon atoms, and more preferably an alkyl group having 1 to 3 carbon atoms.

A compound represented by general formula (V) is preferably a compound represented by formula (V-55).

[Chem. 19]

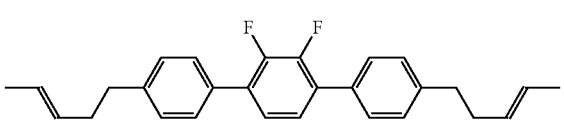
(V-55)

Preferably, the liquid crystal composition further contains one or two or more compounds represented by general formula (Np-1) or (Np-2).

[Chem. 20]

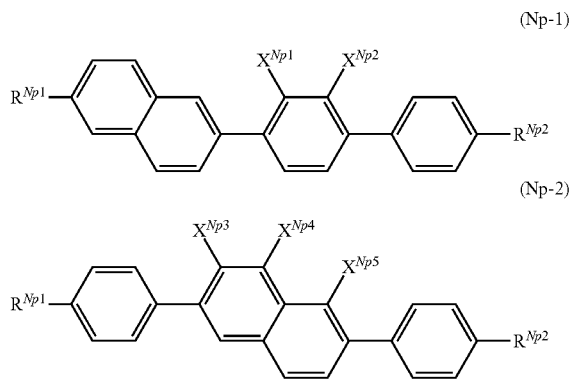

In each of the formulae, $R^{Np1}$ and $R^{Np2}$ each independently represent an alkyl group having 1 to 5 carbon atoms, an alkoxyl group having 1 to 5 carbon atoms, an alkenyl group having 2 to 5 carbon atoms, or an alkenyloxy group having 2 to 5 carbon atoms, and preferably an alkyl group having 1 to 5 carbon atoms. One —CH$_2$— or two or more nonadjacent —CH$_2$—'s present in the group may be independently replaced with —O— or —S—. One or two or more hydrogen atoms present in the group may be independently replaced with a fluorine atom.

$X^{Np1}$, $X^{Np2}$, $X^{Np3}$, $X^{Np4}$, and $X^{Np5}$ each independently represent a hydrogen atom or a fluorine atom. Preferably, at least one of them represents a fluorine atom. More preferably, at least two of them each represent a fluorine atom.

In the liquid crystal composition of the present invention, the total content of the compounds represented by general formulae (I), (IV-1), (IV-2), (IV-3), (N3), (II), (V), (Np-1), and (Np-2) is preferably 80% by mass or more, preferably 85% by mass or more, preferably 88% by mass or more, preferably 90% by mass or more, preferably 92% by mass or more, preferably 94% by mass or more, preferably 95% by mass or more, preferably 97% by mass or more, preferably 98% by mass or more, and preferably 99% by mass or more.

The liquid crystal composition of the present invention has a dielectric anisotropy (Δε) of −2.0 to −8.0 at 25° C., preferably −2.0 to −6.0, more preferably −2.0 to −5.0, and particularly preferably −2.0 to −4.0.

The liquid crystal composition of the present invention has a refractive index anisotropy (Δn) of 0.08 to 0.14 at 20° C., preferably 0.09 to 0.13 and particularly preferably 0.09 to 0.12. Specifically, in the case of addressing a small cell gap, a refractive index anisotropy (Δn) of 0.10 to 0.13 is preferred. In the case of addressing a large cell gap, a refractive index anisotropy (Δn) of 0.08 to 0.10 is preferred.

The liquid crystal composition of the present invention has a viscosity (η) of 5 to 30 mPa·s at 20° C., preferably 10 to 25 mPa·s, and particularly preferably 10 to 22 mPa·s.

The liquid crystal composition of the present invention has a rotational viscosity (γ1) of 50 to 150 mPa·s at 20° C., preferably 60 to 120 mPa·s, and particularly preferably 60 to 100 mPa·s.

The liquid crystal composition of the present invention has a nematic-isotropic liquid phase transition temperature ($T_{ni}$) of 60° C. to 120° C., preferably 70° C. to 100° C., and particularly preferably 70° C. to 85° C.

The liquid crystal composition of the present invention may contain, for example, a typical nematic liquid crystal, smectic liquid crystal, cholesteric liquid crystal, antioxidant, ultraviolet absorbent, in addition to the foregoing compounds.

The liquid crystal composition of the present invention may contain a polymerizable compound. In this case, the liquid crystal composition may be used in a PSA mode, a PSVA mode, a PS mode, or the like. The polymerizable compound is preferably contained in an amount of 0.01% to 2% by mass. Specifically, the liquid crystal composition of the present invention preferably contains one or two or more polymerizable compounds represented by general formula (RM-1).

[Chem. 21]

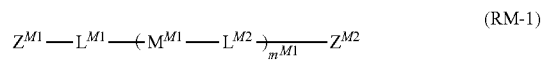

In the formula, $Z^{M1}$ and $Z^{M2}$ each independently represent

[Chem. 22]

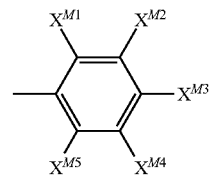

wherein $X^{M1}$ to $X^{M5}$ each represent hydrogen, fluorine, or $$-S^{M1}-R^{M1} \qquad \text{[Chem. 23]}$$

At least one of $X^{M1}$ to $X^{M5}$ in each of $Z^{M1}$ and $Z^{M2}$ preferably represents $$-S^{M1}-R^{M1} \qquad \text{[Chem. 24]}$$

$S^{M1}$ represents an alkyl group having 1 to 12 carbon atoms or a single bond. A methylene group in the alkyl group may be replaced with an oxygen atom, —COO—, —OCO—, or —OCOO—, provided that oxygen atoms are not directly bonded together.

$R^{M1}$ represents one of formulae (R-1) to (R-15):

[Chem. 25]

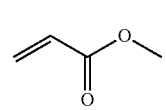

(R-1)

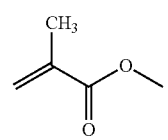

(R-2)

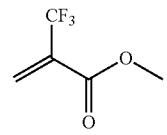

(R-3)

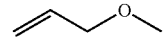

(R-4)

-continued

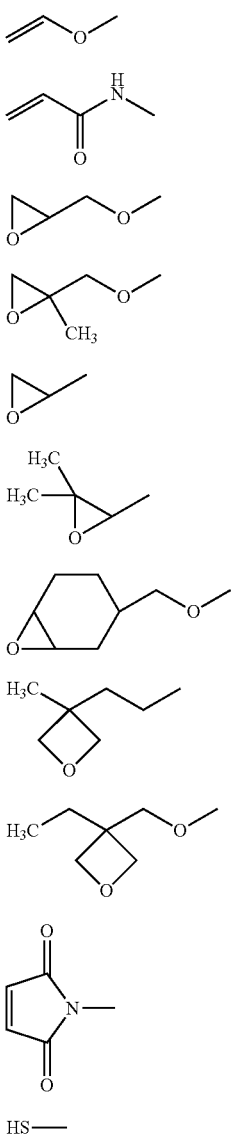

(R-5)
(R-6)
(R-7)
(R-8)
(R-9)
(R-10)
(R-11)
(R-12)
(R-13)
(R-14)
(R-15)

$R^{M1}$ preferably represents formula (R-1) or (R-2).

$L^{M1}$ and $L^{M2}$ each independently represent a single bond, —O—, —CH$_2$—, —OCH$_2$—, —CH$_2$O—, —CO—, —C$_2$H$_4$—, —COO—, —OCO—, —CH=CH—COO—, —COO—CH=CH—, —OCO—CH=CH—, —CH=CH—OCO—, —COOC$_2$H$_4$—, —OCOC$_2$H$_4$—, —C$_2$H$_4$OCO—, —C$_2$H$_4$COO—, —OCOCH$_2$—, —CH$_2$COO—, —CH=CH—, —CF=CH—, —CH=CF—, —CF=CF—, —CF$_2$—, —CF$_2$O—, —OCF$_2$—, —CF$_2$CH$_2$—, —CH$_2$CF$_2$—, —CF$_2$CF$_2$—, or —C≡C—. When a plurality of $L^{M2}$'s are present, they may be the same or different. $L^{M1}$ and $L^{M2}$ each independently preferably represent a single bond, —OCH$_2$—, —CH$_2$O—, —C$_2$H$_4$—, —COO—, —OCO—, —CH=CH—COO—, —COO—CH=CH—, —OCO—CH=CH—, —CH=CH—OCO—, —COOC$_2$H$_4$—, —OCOC$_2$H$_4$—, —C$_2$H$_4$OCO—, —C$_2$H$_4$COO—, —CF$_2$O—, —OCF$_2$—, or —C≡C—, and more preferably a single bond, —C$_2$H$_4$—, —COO—, —OCO—, —CH=CH—COO—, —COO—CH=CH—, —COO—CH=CH—, —CH=CH—OCO—, —COOC$_2$H$_4$—, —OCOC$_2$H$_4$—, or —C$_2$H$_4$COO—.

$M^{M1}$ present represents a 1,4-phenylene group, a 1,4-cyclohexylene group, or a naphthalene-2,6-diyl group. A hydrogen atom in the group may be replaced with a fluorine atom, a chlorine atom, an alkyl group having 1 to 8 carbon atoms, a halogenated alkyl group, a halogenated alkoxy group, an alkoxy group, a nitro group, or $$—S^{M1}—R^{M1}$$ [Chem. 26]

When a plurality of $M^{M1}$'s are present, they may be the same or different. $M^{M1}$ preferably represents an unsubstituted 1,4-phenylene group or a 1,4-phenylene group whose hydrogen atom is replaced with a fluorine atom, an alkyl group having 1 to 8 carbon atoms, or an alkoxy group. In this case, when a plurality of $M^{M1}$'s are present, they may be the same or different.

$m^{M1}$ represents 0, 1, or 2, and preferably 0 or 1. A specific example of the compounds represented by general formula (RM-1), which represents polymerizable compounds, is a compound represented by general formula (RM-1A):

[Chem. 27]

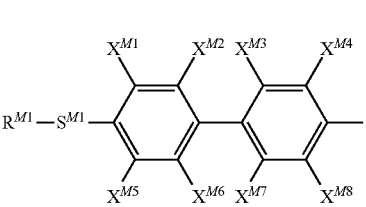

(RM-1A)

(wherein in the formula, $R^{M1}$ and $S^{M1}$ are defined the same as $R^{M1}$ and $S^{M1}$ in general formula (RM-1), and $X^{M1}$ to $X^{M8}$ each represent hydrogen, fluorine, or $$—S^{M1}—R^{M1}$$ [Chem. 28]

In the compound represented by general formula (RM-1A), the foregoing biphenyl skeleton structure is preferably unsubstituted or represented by one of formulae (IV-11) to (IV-14). Preferably, the biphenyl skeleton structure is unsubstituted or represented by formula (IV-11).

[Chem. 29]

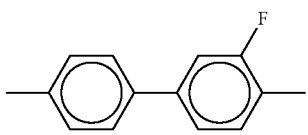

(IV-11)

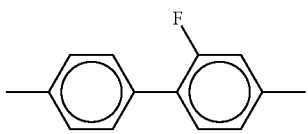

(IV-12)

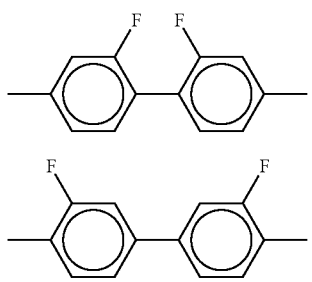

(IV-13)

(IV-14)

The use of the liquid crystal composition that contains the polymerizable compound having the unsubstituted biphenyl skeleton or the biphenyl skeleton represented by one of formulae (IV-11) to (IV-14) optimizes anchoring energy in, for example, a PSA-, PSVA-, or PS-mode liquid crystal display element to provide a good alignment state.

Another example of the compounds represented by general formula (RM-1) is a compound represented by general formula (RM-1B):

[Chem. 30]

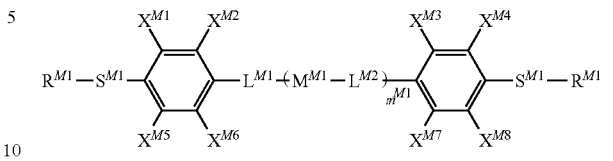

(RM-1B)

(wherein in the formula, $R^{M1}$, $S^{M1}$, $L^{M1}$, $L^{M2}$, $M^{M1}$, and $m^{M1}$ are defined the same as $R^{M1}$, $S^{M1}$, $L^{M1}$, $L^{M2}$, $M^{M1}$, and $m^{M1}$ in general formula (RM-1), and $X^{M1}$ to $X^{M5}$ each represent hydrogen, fluorine, or $$-S^{M1}-R^{M1} \qquad \text{[Chem. 31]}$$

As the compounds represented by general formula (RM-1), which represents polymerizable compounds, specific compounds represented by structural formulae (M1-1) to (M1-13), (M2-1) to (M2-8), (M3-1) to (M3-6), (M4-1) to (M4-7), and (I-1) to (I-40) illustrated below are preferred.

[Chem. 32]

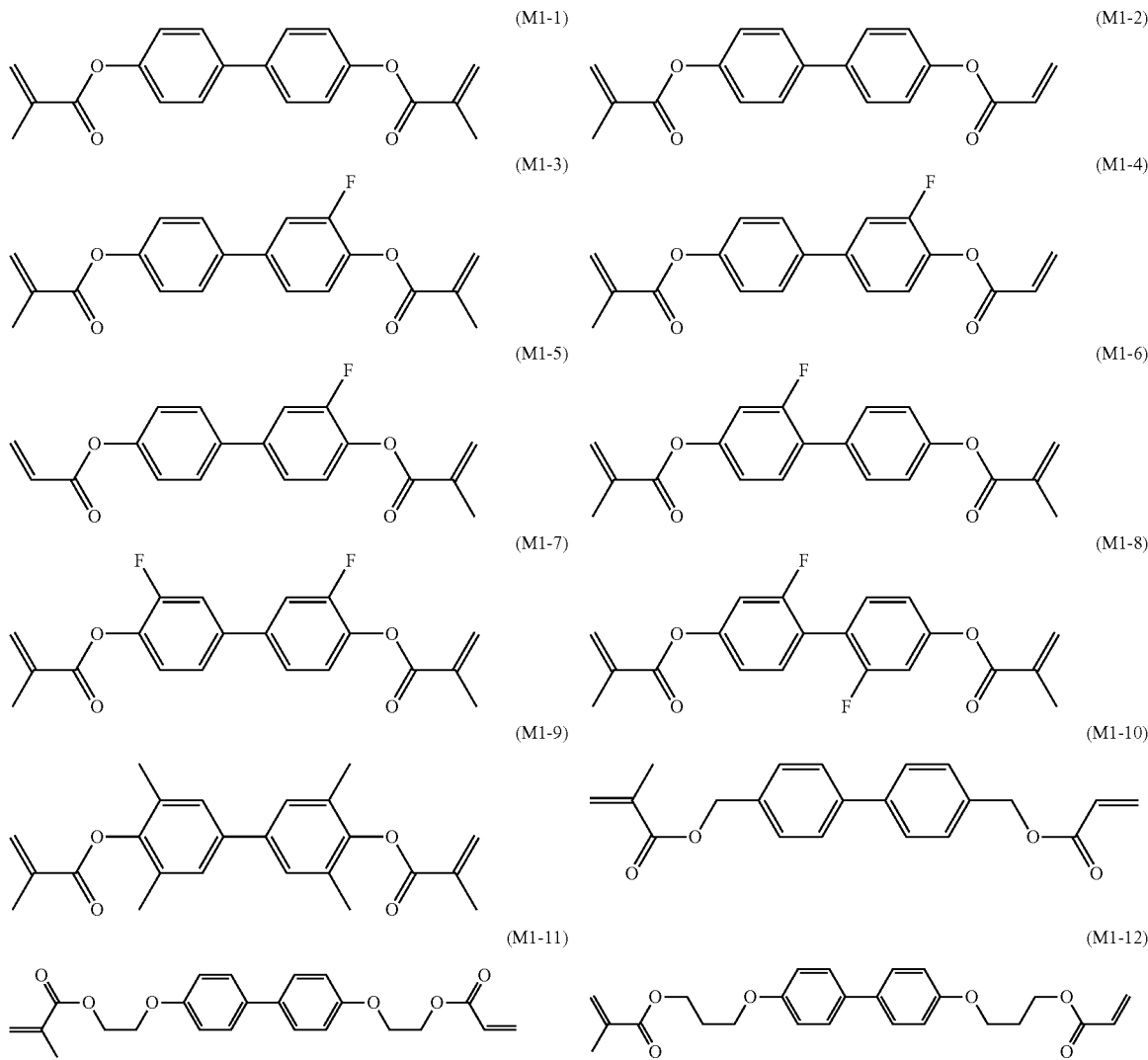

-continued
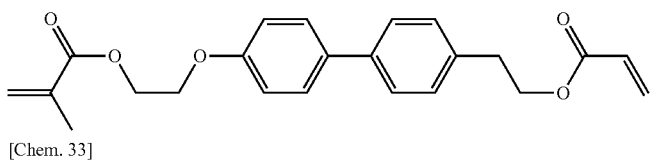
(M1-13)
[Chem. 33]
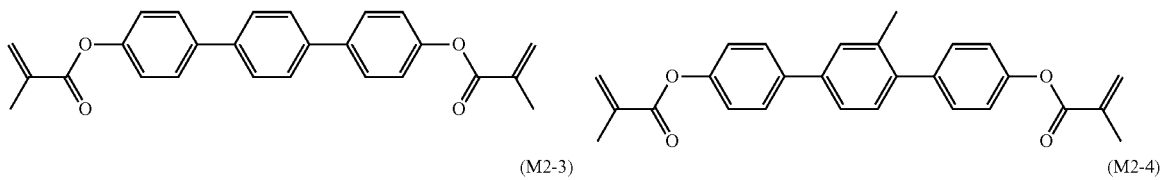
(M2-1) (M2-2)
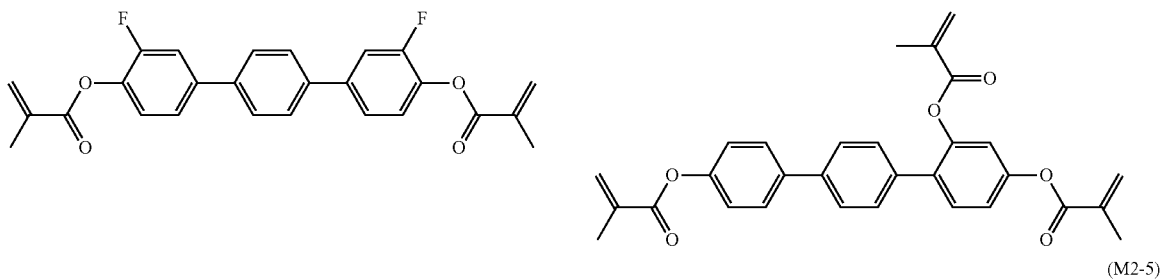
(M2-3) (M2-4)
(M2-5)
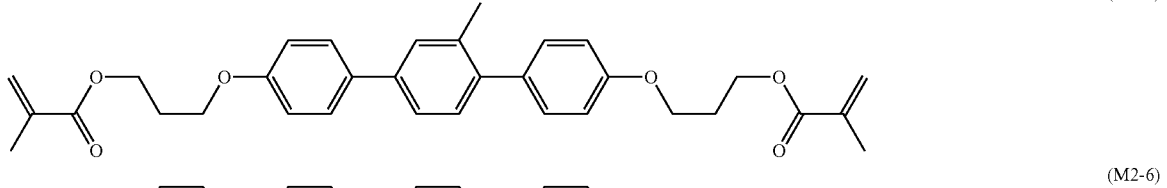
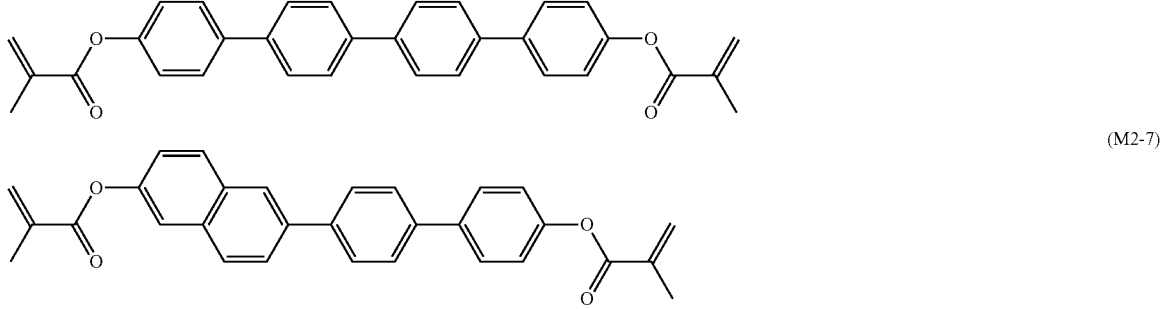
(M2-6)
(M2-7)
(M2-8)
[Chem. 34]
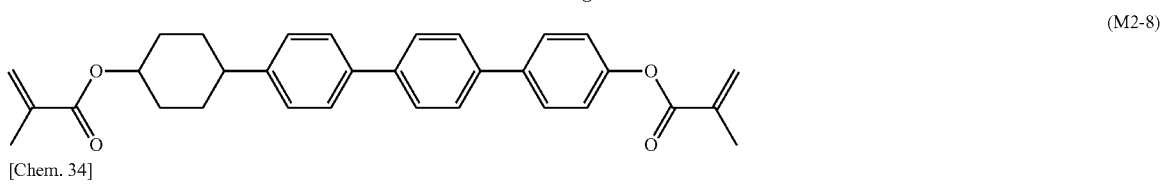
(M3-1) (M3-2)
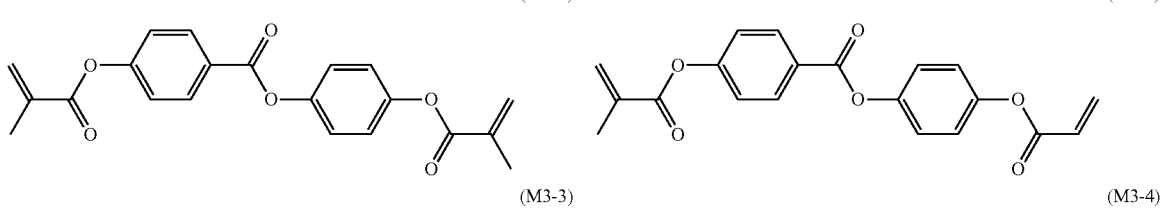
(M3-3) (M3-4)
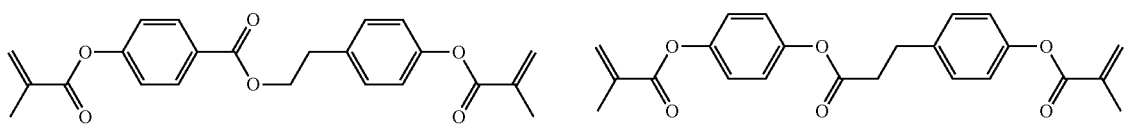

-continued
(M3-5)
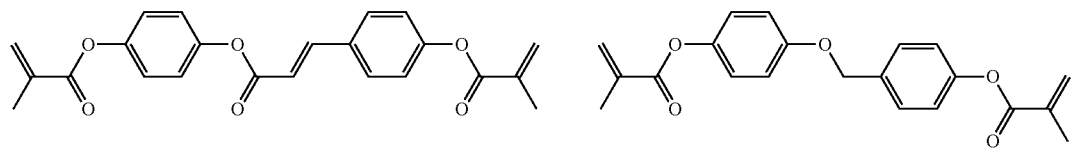
(M3-6)
[Chem. 35]
(M4-1)
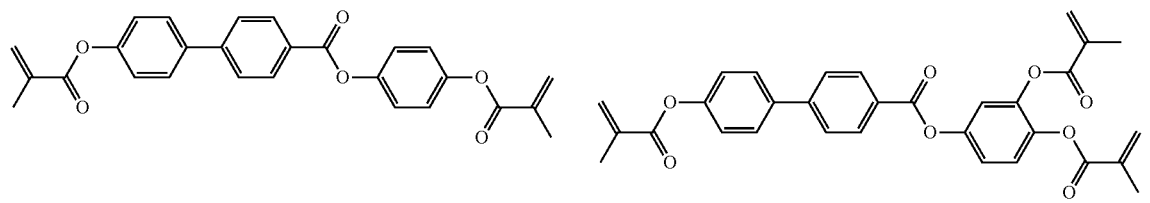
(M4-2)
(M4-3)
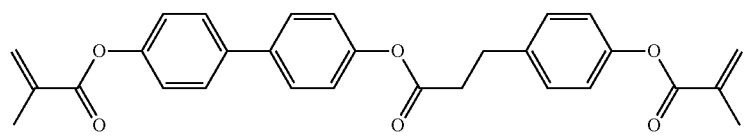
(M4-4)
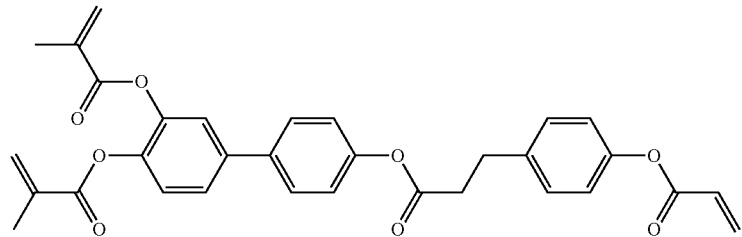
(M4-5)
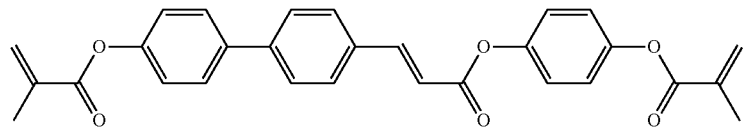
(M4-6)
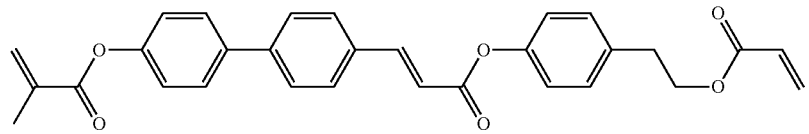
(M4-7)
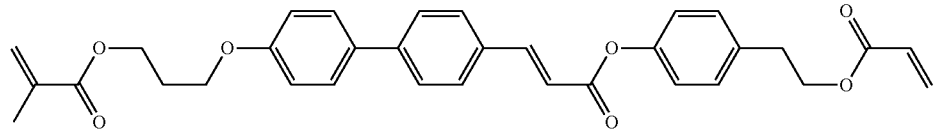
[Chem. 36]
(I-1)
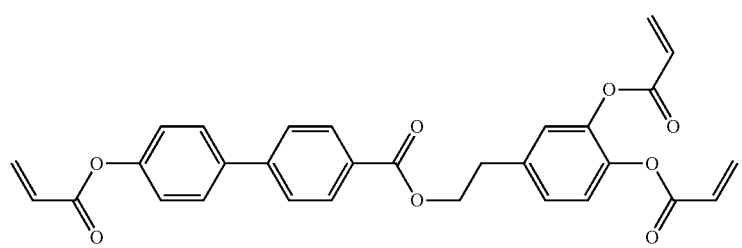

-continued
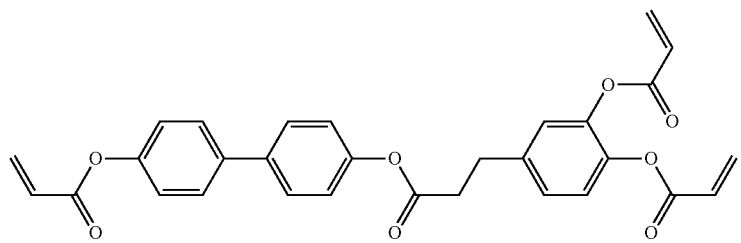
(I-2)
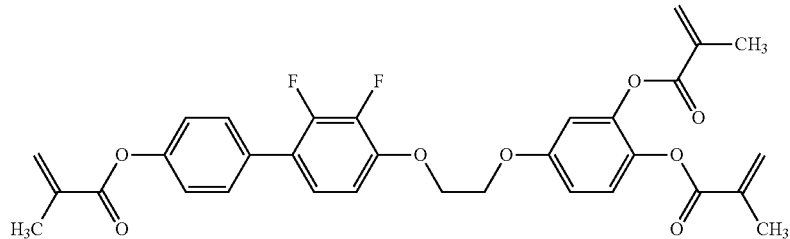
(I-3)
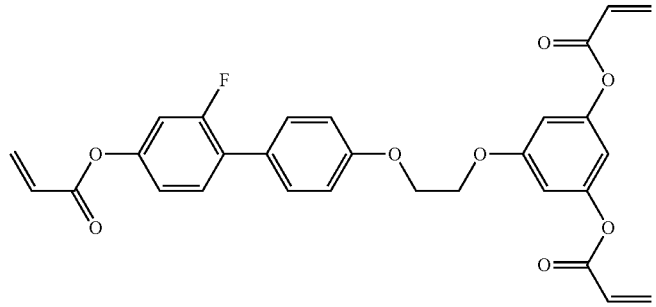
(I-4)
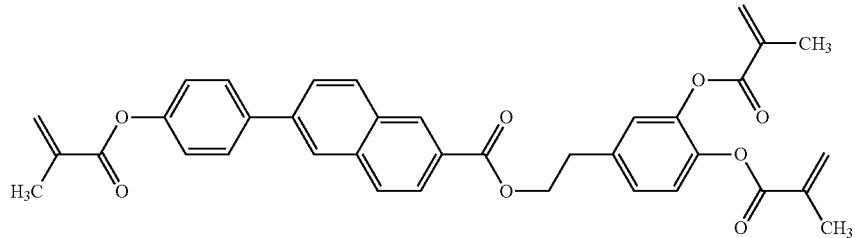
(I-5)
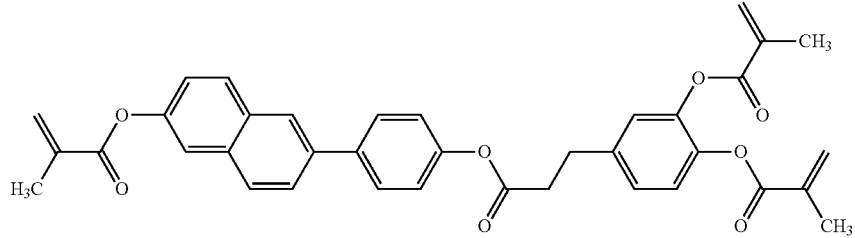
(I-6)
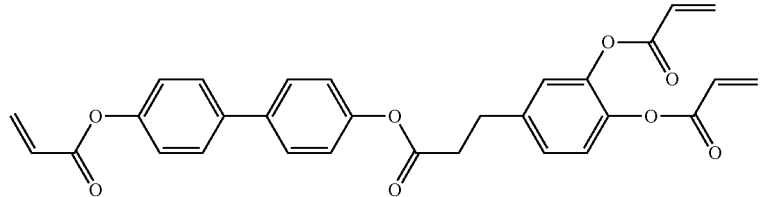
(I-7)

-continued
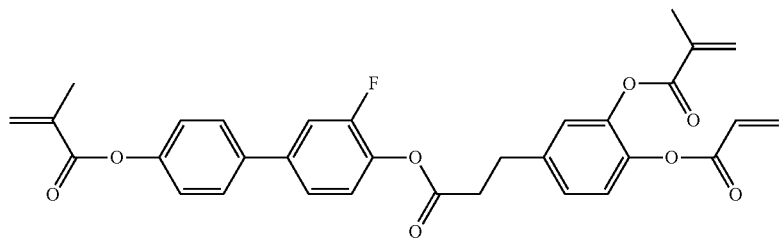
(I-8)
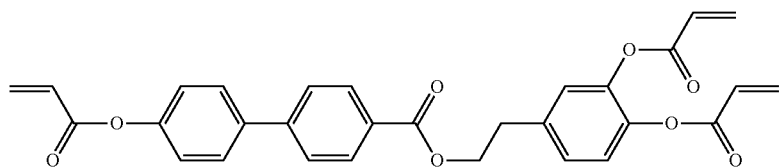
(I-9)
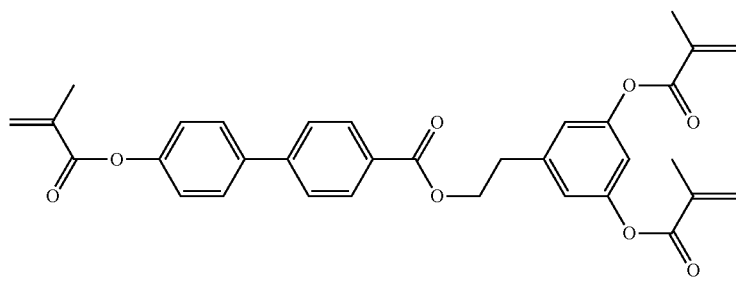
(I-10)
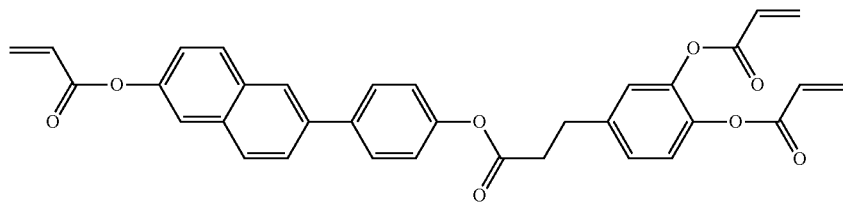
(I-11)
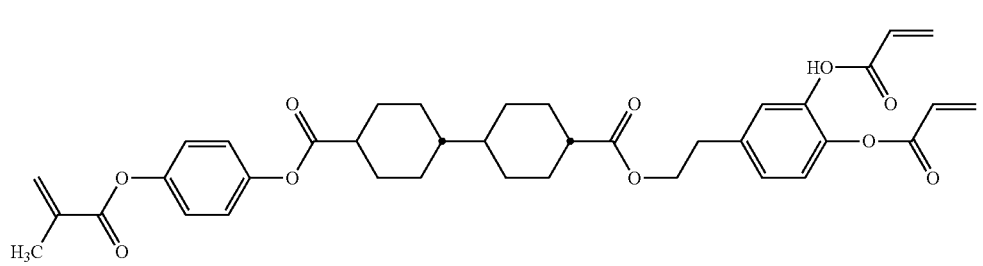
(I-12)
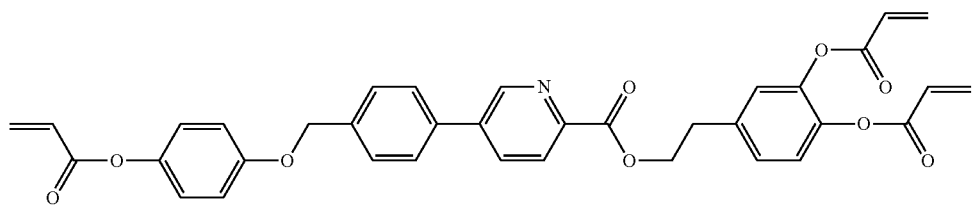
(I-13)

-continued
(I-14)
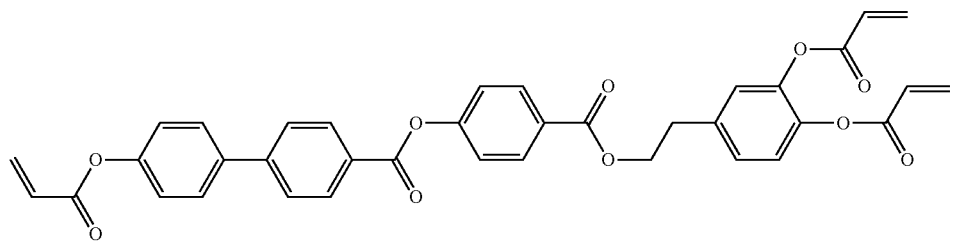
[Chem. 38]
(I-15)
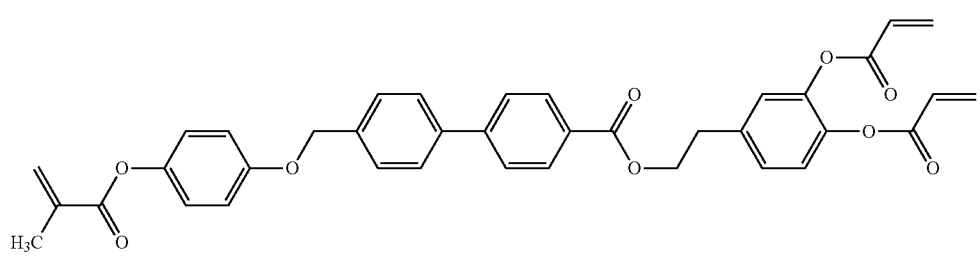
(I-16)
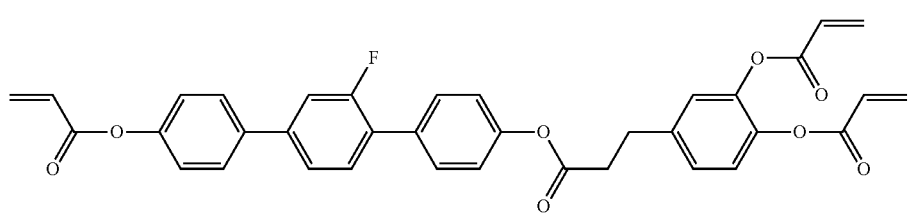
(I-17)
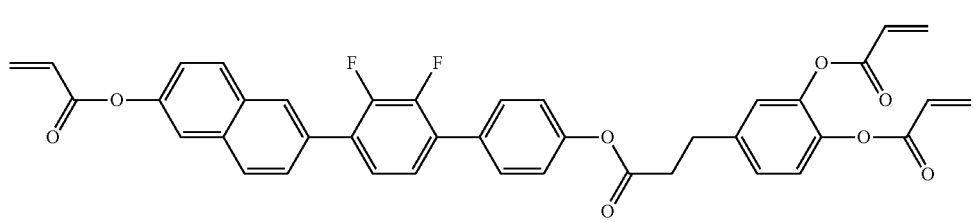
(I-18)
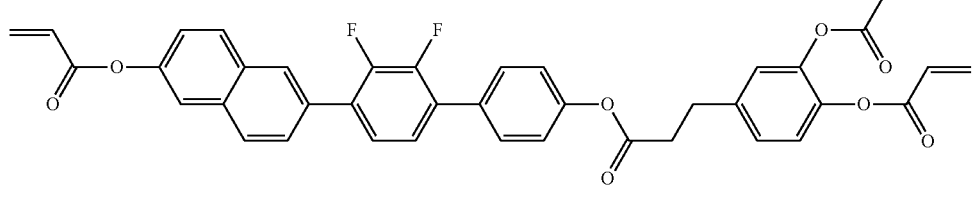
(I-19)
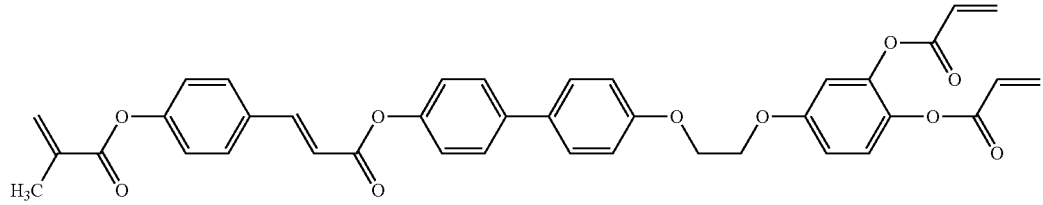
(I-20)
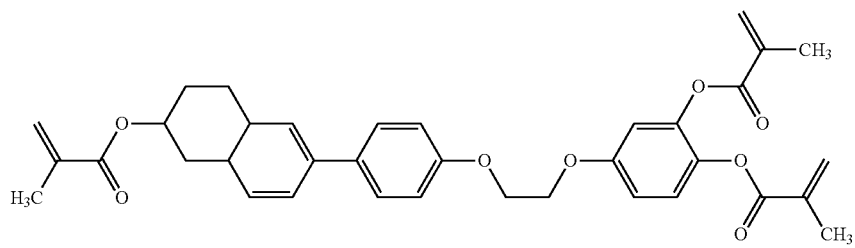

-continued
[Chem. 39]
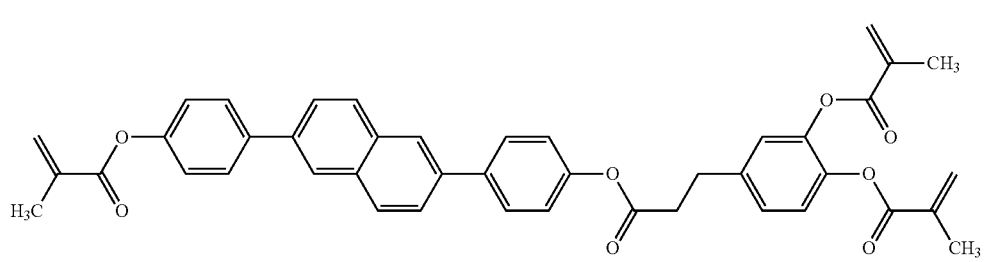
(I-21)
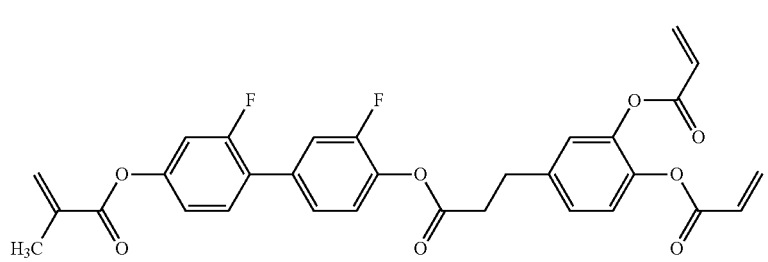
(I-22)
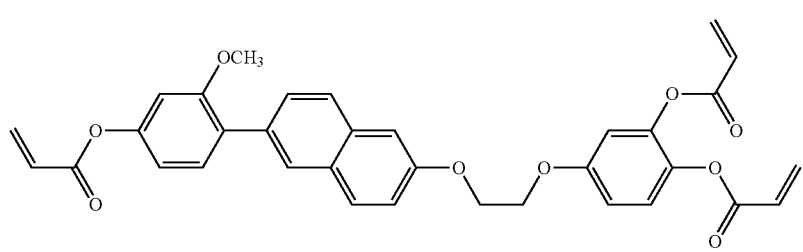
(I-23)
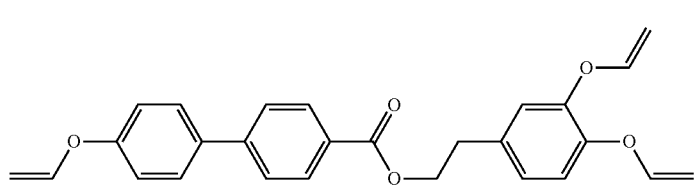
(I-24)
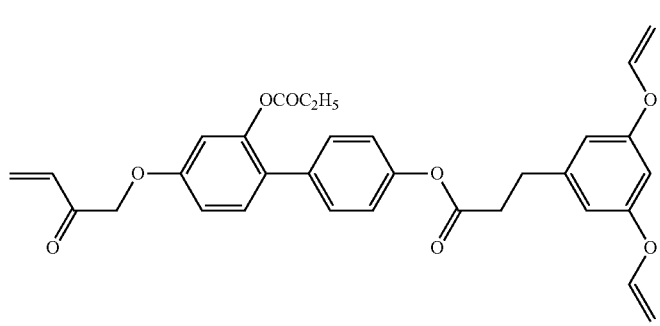
(I-25)
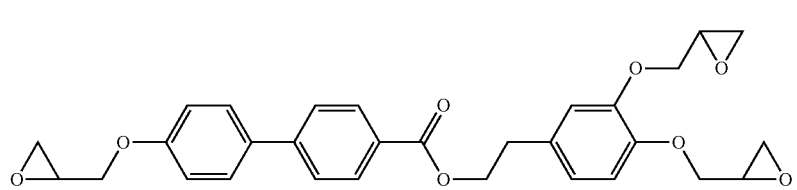
(I-26)

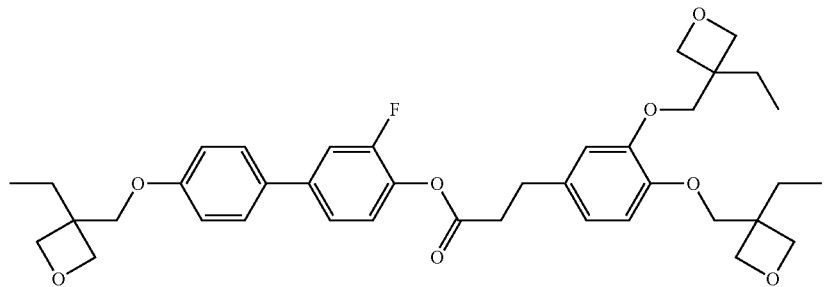
(I-27)
[Chem. 40]
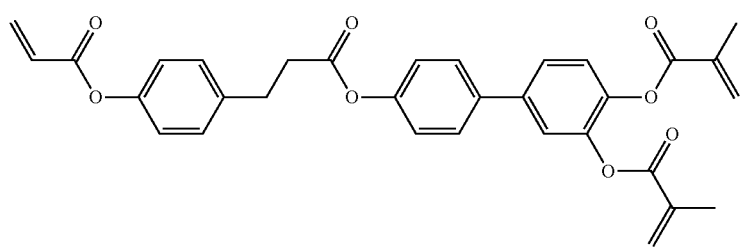
(I-28)
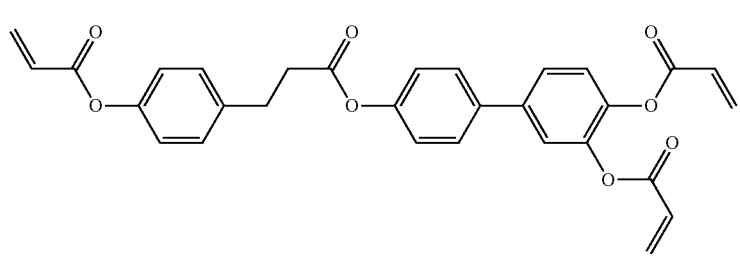
(I-29)
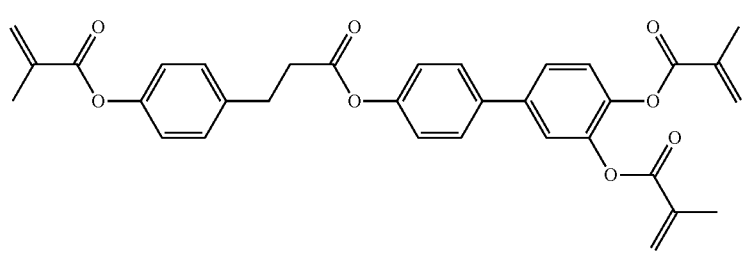
(I-30)
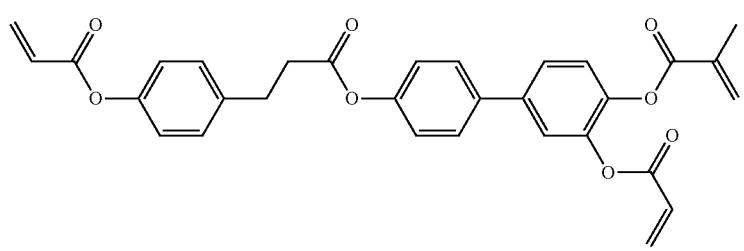
(I-31)
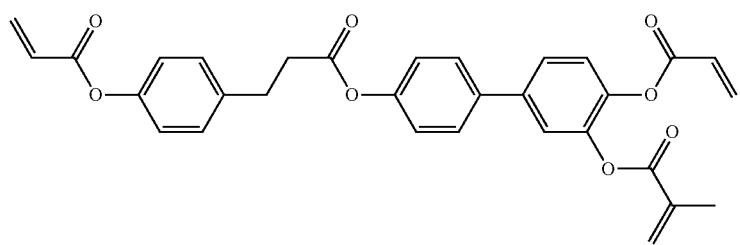
(I-32)

-continued
[Chem. 41]
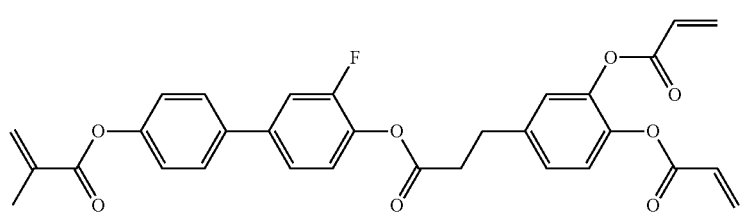
(I-33)
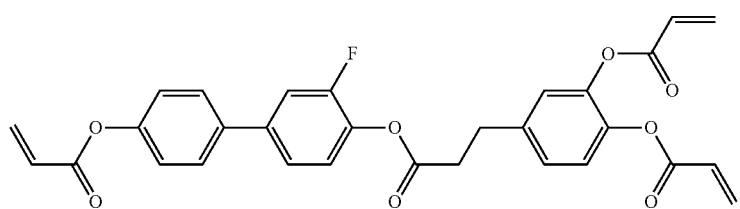
(I-34)
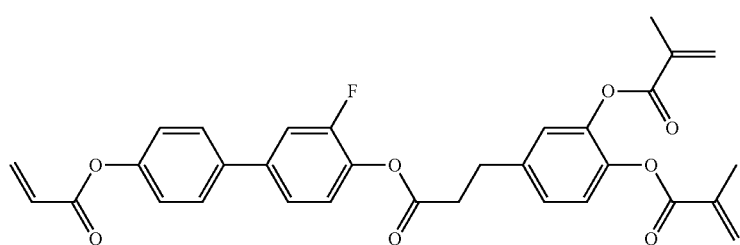
(I-35)
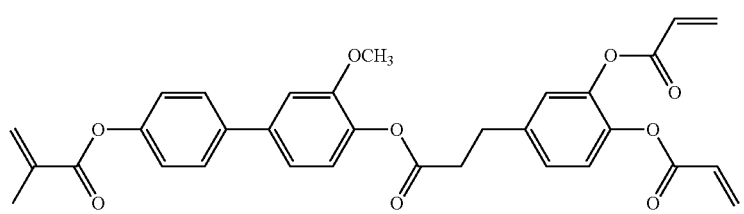
(I-36)
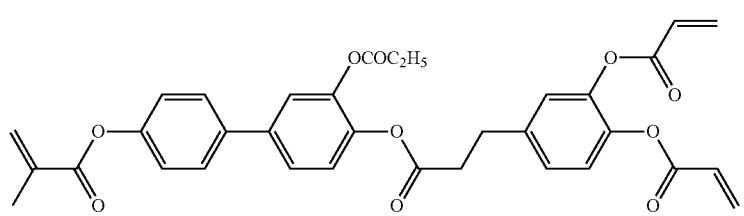
(I-37)
[Chem. 42]
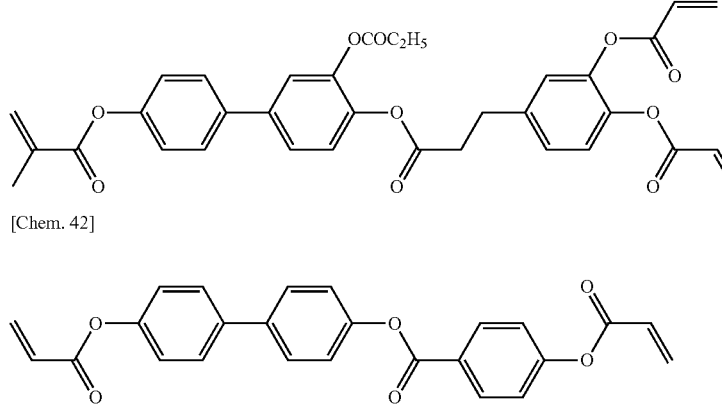
(I-38)
[Chem. 43]
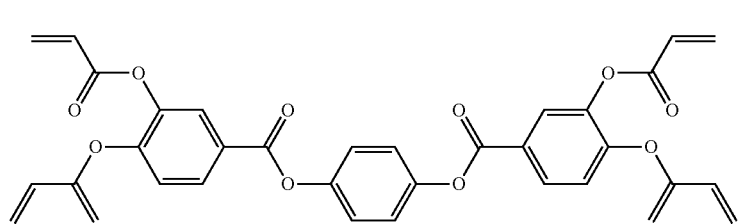
(I-39)

[Chem. 44]

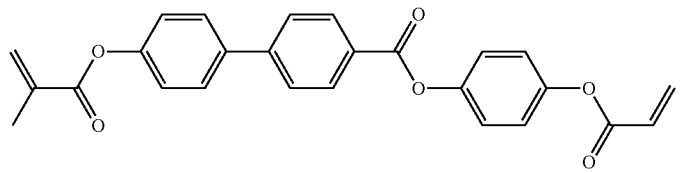

(I-40)

More preferred are the compounds represented by (M1-1) to (M1-8), (M1-10) to (M1-13), (M2-2) to (M2-5), (M3-1), (M3-4), (M3-5), (M4-1), (M4-2), (M4-4), (M4-6), (M4-7), (I-1) to (I-11), (1-22) to (1-25), and (1-28) to (I-40).

Particularly preferred are the compounds represented by (M1-1), (M1-3), (M1-6) to (M1-8), (M1-11), (M1-12), (M2-2), (M2-4), (M3-1), (M3-5), (M4-2), (M4-6), (M4-7), and (1-33) to (1-37).

A polymerizable compound-containing liquid crystal composition that contains both of a compound represented by general formula (I) and a compound represented by general formula (RM-1), which represents the polymerizable compound, has low viscosity ($\eta$), low rotational viscosity ($\gamma 1$), a large elastic constant ($K_{33}$), and a high VHR. Thus, in the case of a PSA- or PSVA-mode liquid crystal display element including the liquid crystal composition, both a fast response and high reliability are achieved. Therefore, it is preferable to contain both of the compounds. More preferably, compounds represented by general formulae (I) and (N-3) and a polymerizable compound represented by general formula (RM-1) are all contained. More preferably, compounds represented by general formulae (I), (N-3), and (II) and the polymerizable compound represented by general formula (RM-1) are all contained. More preferably, the compounds represented by general formulae (I), (N-3), and (II), a compound selected from the group consisting of general formulae (IV-1) to (IV-3), and the polymerizable compound represented by general formula (RM-1) are all contained. More preferably, compounds represented by general formulae (I), (N-3), (II), and (V), the compound selected from the group consisting of general formulae (IV-1) to (IV-3), and the polymerizable compound represented by general formula (RM-1) are all contained. More preferably, compounds represented by general formulae (I), (N-3), (II), (Np-1), and (Np-2), the compound selected from the group consisting of general formulae (IV-1) to (IV-3), and the polymerizable compound represented by general formula (RM-1) are all contained. More preferably, the compounds represented by general formulae (I), (N-3), (II), (V), (Np-1), and (Np-2), the compound selected from the group consisting of general formulae (IV-1) to (IV-3), and the polymerizable compound represented by general formula (RM-1) are all contained.

The liquid crystal display element including the liquid crystal composition of the present invention has a remarkable characteristic of its fast response, is particularly useful for an active matrix-addressed liquid-crystal display element, and can be used in a VA, PSVA, PSA, IPS, or ECB mode.

EXAMPLES

While the present invention will be described in more detail below by examples, the present invention is not limited to these examples. In compositions of examples and comparative examples, "%" indicates "% by mass".

In descriptions of compounds in the examples, the following symbols are used.

(Side Chain)
-n —$C_nH_{2n+1}$ linear alkyl group having n carbon atoms
n- $C_nH_{2n+1}$— linear alkyl group having n carbon atoms
-On —$OC_nH_{2n+1}$ linear alkoxy group having n carbon atoms
nO- $C_nH_{2n+1}O$— linear alkoxy group having n carbon atoms
—V —CH=$CH_2$
V— $CH_2$=CH—
—V1 —CH=CH—$CH_3$
1V— $CH_3$—CH=CH—
-2V —$CH_2$—$CH_2$—CH=$CH_3$
V2- $CH_3$=CH—$CH_2$—$CH_2$—
-2V1 —$CH_2$—$CH_2$—CH=CH—$CH_3$
1V2- $CH_3$—CH=CH—$CH_2$—$CH_2$
(Ring Structure)

[Chem. 45]

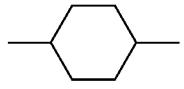

Cy

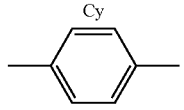

Ph

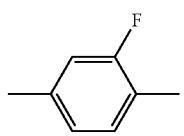

Ph1

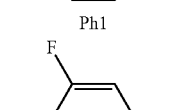

Ph2

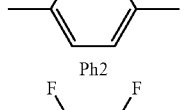

Ph5

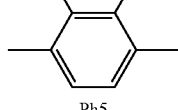

Ph6

-continued

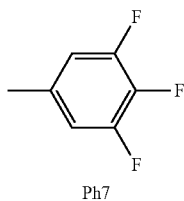
Ph7

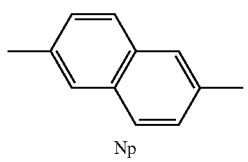
Np

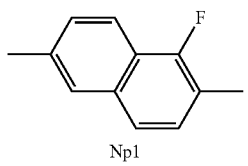
Np1

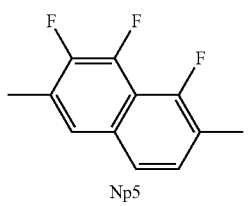
Np5

In the examples, the following properties are measured.
$T_{ni}$: nematic-isotropic liquid phase transition temperature (° C.)
$T_{cn}$: solid-nematic phase transition temperature (° C.)
Δn: refractive index anisotropy at 20° C.
Δε: dielectric anisotropy at 20° C.
η: viscosity (mPa·s) at 20° C.
γ1: rotational viscosity (mPa·s) at 20° C.
$K_{33}$: elastic constant ($K_{33}$) (pN) at 20° C.
Pretilt angle before polymerization: pretilt angle (°) before UV irradiation
Pretilt angle after polymerization: pretilt angle (°) after UV irradiation In the case where a pretilt angle was formed in a test cell, the test cell was irradiated with UV at 60 J (365 nm) while a rectangular voltage of 10 V and 100 Hz were applied to the test cell. AS a UV light source, a Multilight manufactured by Ushio Inc. was used.

The response speed of a sample was measured with a test cell having a thickness of 3.5 μm and including JALS2096 serving as an alignment layer, and DMS301 available from AUTRONIC-MELCHERS at a Vsel of 5 V, a Vnsel of 1 V, and a measurement temperature of 20° C.

Comparative Example 1, Examples 1 to 6

Liquid crystal compositions of LC-A (Comparative example 1), LC-1 (Example 1), LC-2 (Example 2), LC-3 (Example 3), LC-4 (Example 4), LC-5 (Example 5), and LC-6 (Example 6) were prepared, and values of physical properties thereof were measured. Table 1 lists the structures of the liquid crystal compositions and the measured values of the physical properties.

TABLE 1

|  | Comparative example 1 LC-A | Example 1 LC-1 | Example 2 LC-2 | Example 3 LC-3 | Example 4 LC-4 | Example 5 LC-5 | Example 6 LC-6 |
| --- | --- | --- | --- | --- | --- | --- | --- |
| 3-Ph—1O—Ph5—O2 general formula (I) |  |  |  |  | 3 |  |  |
| 2-Ph—Ph—1O—Ph5—O2 general formula (I) |  | 5 | 3 | 3 | 5 |  |  |
| 2-Ph—Ph—1O—Ph5—O3 general formula (I) |  |  |  | 3 |  |  |  |
| 3-Ph—Ph—1O—Ph5—O2 general formula (I) |  |  | 5 | 5 |  | 5 | 5 |
| 4-Ph—Ph—1O—Ph5—O2 general formula (I) |  |  |  | 3 |  |  |  |
| 3-Ph—Ph1—1O—Ph5—O2 general formula (I) |  |  |  |  |  | 3 |  |
| 3-Ph—Ph5—1O—Ph5—O2 general formula (I) |  |  |  |  |  |  | 3 |
| 3-Cy—1O—Ph5—O1 general formula (II-A1) |  |  | 2.5 |  |  | 2.5 | 2.5 |
| 3-Cy—1O—Ph5—O2 general formula (II-A1) | 13 | 7 |  | 2 | 4 |  |  |
| 1V—Cy—1O—Ph5—O2 general formula (II-A1) | 8 | 8 | 13 | 13 | 8 | 13 | 13 |
| 3-Cy—Cy—1O—Ph5—O2 general formula (II-A3) |  |  | 5 | 2 |  | 5 | 5 |
| V—Cy—Cy—1O—Ph5—O2 general formula (II-A3) | 10 | 11 |  |  | 11 |  |  |
| 1V—Cy—Cy—1O—Ph5—O2 general formula (II-A3) | 10 | 10 | 13 | 13 | 10 | 13 | 13 |
| 3-Cy—Cy—V general formula (IV-1) |  |  |  | 20 |  |  |  |
| 2-Cy—Cy—V1 general formula (IV-1) | 20 | 28 | 30.5 | 11.5 | 28 | 30.5 | 30.5 |
| 3-Cy—Cy—V1 general formula (IV-1) | 8 | 8 | 8 | 10 | 8 | 8 | 8 |
| 3-Ph—Ph-1 general formula (IV-3) | 10 | 8 | 6.5 | 4 | 8 | 6.5 | 6.5 |
| 3-Cy—Cy—Ph-1 general formula (N3-1) | 7.5 | 2 | 4 | 2 | 2 | 4 | 4 |
| 3-Cy—Ph—Ph-2 general formula (N3-3) | 6.5 | 6 | 5 | 6.5 | 6 | 5 | 5 |
| 5-Cy—Ph—Ph-2 general formula (N3-3) | 5 | 5 | 2.5 |  | 5 | 2.5 | 2.5 |
| 3-Np—Ph5—Ph-2 general formula (Np-1) | 2 | 2 | 2 | 2 | 2 | 2 | 2 |
| Total | 100 | 100 | 100 | 100 | 100 | 100 | 100 |
| Tni [° C.] | 75 | 76 | 75 | 76 | 74 | 74 | 75 |
| Tcn [° C.] | −57 | −35 | −30 | −28 | −37 | −32 | −30 |
| Δn | 0.108 | 0.108 | 0.108 | 0.108 | 0.109 | 0.108 | 0.108 |
| η [mPa·s] | 15.4 | 14.9 | 15.0 | 14.7 | 15.0 | 15.1 | 15.0 |
| $γ_1$ [mPa·s] | 114 | 106 | 112 | 107 | 105 | 112 | 113 |
| Δε | −3.2 | −3.0 | −3.1 | −3.1 | −3.0 | −3.1 | −3.2 |
| $K_{33}$ [pN] | 16.0 | 16.1 | 16.2 | 16.0 | 16.0 | 16.1 | 16.2 |
| $γ_1/K_{33}$ | 7.1 | 6.6 | 6.9 | 6.7 | 6.6 | 7.0 | 7.0 |

Each of the liquid crystal compositions LC-1, LC-2, LC-3, LC-4, LC-5, and LC-6 of the present invention had low viscosity ($\eta$), low rotational viscosity ($\gamma 1$), and a large elastic constants ($K_{33}$), and the value of $\gamma 1/K_{33}$ was smaller than that of LC-A of the comparative example.

The measurement results of the response speed of liquid crystal display elements including the liquid crystal compositions revealed that LC-1, LC-2, LC-3, LC-4, LC-5, and LC-6 had sufficiently fast responses and that their response speeds were higher than LC-A by 5% or more.

The results demonstrated that each of the liquid crystal compositions of the present invention had sufficiently low viscosity ($\eta$), sufficiently low rotational viscosity ($\gamma 1$), a large elastic constant ($K_{33}$), and a negative dielectric anisotropy ($\Delta\epsilon$) whose absolute value was large, without reducing the refractive index anisotropy ($\Delta n$) or the nematic-isotropic liquid phase transition temperature ($T_{ni}$) and that thus, for example, the VA-mode liquid crystal display elements including the liquid crystal compositions had excellent display quality and high response speeds.

Comparative Example 2 and Examples 7 to 15

Liquid crystal compositions MLC-A (Comparative example 2), MLC-1-1 (Example 7), MLC-1-2 (Example 8), MLC-1-3 (Example 9), MLC-1-4 (Example 10), MLC-2 (Example 11), MLC-3 (Example 12), MLC-4 (Example 13), MLC-5 (Example 14), and MLC-6 (Example 15) were prepared. Each of the liquid crystal compositions was vacuum-injected into a test cell. Then the pretilt angle was measured before and after UV irradiation. Table 2 lists the structures of the liquid crystal compositions and the measurement results of their pretilt angles.

As with MLC-A, the UV irradiation imparted appropriate pretilt angles to the liquid crystal compositions MLC-1-1 to MLC-1-4 and MLC-2 to MLC-2-6 of the present invention. The measurement results of response speeds of liquid crystal display elements including the liquid crystal compositions revealed that MLC-1-1 to MLC-1-4 and MLC-2 to MLC-6 had sufficiently fast responses and that their response speeds were higher than MLC-A by 5% or more.

The results demonstrated that each of the liquid crystal compositions of the present invention had sufficiently low viscosity ($\eta$), sufficiently low rotational viscosity ($\gamma 1$), a large elastic constant ($K_{33}$), and a negative dielectric anisotropy ($\Delta\epsilon$) whose absolute value was large, without reducing the refractive index anisotropy ($\Delta n$) or the nematic-isotropic liquid phase transition temperature ($T_{ni}$) and that thus, for example, the VA-, PSA-, and PSVA-mode liquid crystal display elements including the liquid crystal compositions had excellent display quality and high response speeds.

Comparative Example 3 and Examples 16 and 17

Liquid crystal compositions LC-B (Comparative example 3), LC-7 (Example 16), and LC-8 (Example 17) were prepared. Values of physical properties thereof were measured. Table 3 lists the structures of the liquid crystal compositions and the measured values of the physical properties.

TABLE 2

|  | Comparative example 2 | Example 7 | Example 8 | Example 9 | Example 10 | Example 11 | Example 12 | Example 13 | Example 14 | Example 15 |
|---|---|---|---|---|---|---|---|---|---|---|
|  | MLC-A | MLC-1-1 | MLC-1-2 | MLC-1-3 | MLC-1-4 | MLC-2 | MLC-3 | MLC-4 | MLC-5 | MLC-6 |
| LC-A | 99.7 | | | | | | | | | |
| LC-1 | | 99.7 | 99.7 | 99.7 | 99.7 | | | | | |
| LC-2 | | | | | | 99.7 | | | | |
| LC-3 | | | | | | | 99.7 | | | |
| LC-4 | | | | | | | | 99.7 | | |
| LC-5 | | | | | | | | | 99.7 | |
| LC-6 | | | | | | | | | | 99.7 |
| Polymerizable compound formula (M1-1) | | 0.3 | | | | | | | | |
| Polymerizable compound formula (M1-3) | 0.3 | | 0.3 | 0.25 | | 0.3 | 0.3 | 0.3 | | 0.3 |
| Polymerizable compound formula (M4-7) | | | | 0.05 | | | | | | |
| Polymerizable compound formula (I-33) | | | | | 0.3 | | | | 0.3 | |
| Total | 100 | | 100 | 100 | 100 | 100 | 100 | 100 | 100 | 100 |
| Pretilt angle before polymerization [°] | 88.7 | 88.8 | 88.5 | 88.9 | 88.7 | 88.6 | 88.7 | 88.8 | 88.9 | 88.5 |
| Pretilt angle before polymerization [°] | 85.5 | 83.0 | 82.9 | 83.2 | 81.5 | 85.3 | 83.2 | 81.1 | 78.0 | 82.3 |

TABLE 3

|  | Comparative example 3 LC-B | Example 16 LC-7 | Example 17 LC-8 |
|---|---|---|---|
| 2-Ph—Ph—1O—Ph5—O2 general formula (I) |  |  | 3 |
| 3-Ph—Ph—1O—Ph5—O2 general formula (I) |  | 5 | 6 |
| 3-Cy—1O—Ph5—O2 general formula (II-A1) | 11 | 8 | 8 |
| 2-Cy—Cy—1O—Ph5—O2 general formula (II-A3) | 6 | 8 | 4 |
| 3-Cy—Cy—1O—Ph5—O2 general formula (II-A3) | 11 | 12 | 10 |
| 3-Cy—Ph—Ph5—O2 general formula (II-B4) | 7 | 5 | 7 |
| 3-Cy—Ph—Ph5—O3 general formula (II-B4) | 8 | 8 | 8 |
| 3-Cy—Ph—Ph5—O4 general formula (II-B4) | 6 | 3 | 6 |
| 3-Cy—Cy-2 general formula (IV-1) | 18 | 21 | 26 |
| 3-Cy—Cy-4 general formula (IV-1) | 8 | 8 | 8 |
| 3-Cy—Ph—O1 general formula (IV-2) | 4 | 4 | 4 |
| 3-Ph—Ph-1 general formula (IV-3) | 11 | 10 | 5 |
| 3-Cy—Cy—Ph-1 general formula (N3-1) | 5 | 3 |  |
| 3-Ph—Ph5—Ph-2 general formula (V) | 5 | 5 | 5 |
| Total | 100 | 100 | 100 |
| Tni [° C.] | 75 | 75 | 75 |
| Tcn [° C.] | −35 | −33 | −32 |
| Δn | 0.108 | 0.108 | 0.108 |
| η [mPa · s] | 17.2 | 16.8 | 16.5 |
| $\gamma_1$ [mPa · s] | 118 | 114 | 112 |
| Δε | −3.1 | −3.1 | −3.1 |
| K33 [pN] | 13.0 | 13.2 | 13.3 |
| $\gamma_1/K_{33}$ | 9.1 | 8.6 | 8.4 |

Each of the liquid crystal compositions LC-7 and LC-8 of the present invention had low viscosity (η), low rotational viscosity (γ1), and a large elastic constant ($K_{33}$), and the value of $\gamma_1/K_{33}$ was smaller than that of LC-B of the comparative example.

The measurement results of the response speed of liquid crystal display elements including the liquid crystal compositions revealed that LC-7 and LC-8 had sufficiently fast responses and that their response speeds were higher than LC-B by 8% or more.

The results demonstrated that each of the liquid crystal compositions of the present invention had sufficiently low viscosity (η), sufficiently low rotational viscosity (γ1), a large elastic constant ($K_{33}$), and a negative dielectric anisotropy (Δε) whose absolute value was large, without reducing the refractive index anisotropy (Δn) or the nematic-isotropic liquid phase transition temperature ($T_{ni}$) and that thus, for example, the VA-mode liquid crystal display elements including the liquid crystal compositions had excellent display quality and high response speeds.

Comparative Example 4 and Examples 18 and 19

Liquid crystal compositions MLC-B (Comparative example 4), MLC-7 (Example 18), and MLC-8 (Example 19) were prepared. Each of the liquid crystal compositions was vacuum-injected into a test cell. Then the pretilt angle was measured before and after UV irradiation. Table 4 lists the structures of the liquid crystal compositions and the measurement results of their pretilt angles.

TABLE 4

|  | Comparative example 4 MLC-B | Example 18 MLC-7 | Example 19 MLC-8 |
|---|---|---|---|
| LC-B | 99.7 |  |  |
| LC-4 |  | 99.7 |  |
| LC-5 |  |  | 99.7 |
| Polymerizable compound formula (M1-3) | 0.3 | 0.3 | 0.3 |
| Total | 100 | 100 | 100 |
| Pretilt angle before polymerization [°] | 88.8 | 88.6 | 88.7 |
| Pretilt angle before polymerization [°] | 84.3 | 84.0 | 84.5 |

As with MLC-B, the UV irradiation imparted appropriate pretilt angles to the liquid crystal compositions MLC-7 and MLC-8 of the present invention. The measurement results of response speeds of liquid crystal display elements including the liquid crystal compositions revealed that MLC-7 and MLC-8 had sufficiently fast responses and that their response speeds were higher than MLC-B by 8% or more.

The results demonstrated that each of the liquid crystal compositions of the present invention had sufficiently low viscosity (η), sufficiently low rotational viscosity (γ1), a large elastic constant ($K_{33}$), and a negative dielectric anisotropy (Δε) whose absolute value was large, without reducing the refractive index anisotropy (Δn) or the nematic-isotropic liquid phase transition temperature ($T_{ni}$) and that thus, for example, the VA-, PSA-, and PSVA-mode liquid crystal display elements including the liquid crystal compositions had excellent display quality and high response speeds.

Comparative Example 5 and Examples 20 to 22

Liquid crystal compositions LC-C(Comparative example 5), LC-9 (Example 20), LC-10 (Example 21), and LC-11 (Example 22) were prepared. Values of physical properties thereof were measured. Table 5 lists the structures of the liquid crystal compositions and the measured values of the physical properties.

The results demonstrated that each of the liquid crystal compositions of the present invention had sufficiently low viscosity ($\eta$), sufficiently low rotational viscosity ($\gamma 1$), a large elastic constant ($K_{33}$), and a negative dielectric anisotropy ($\Delta\varepsilon$) whose absolute value was large, without reducing the refractive index anisotropy ($\Delta n$) or the nematic-isotropic liquid phase transition temperature ($T_{ni}$) and that thus, for example, the VA-mode liquid crystal display elements including the liquid crystal compositions had excellent display quality and high response speeds.

TABLE 5

|  | Comparative example 5 LC-C | Example 20 LC-9 | Example 21 LC-10 | Example 22 LC-11 |
|---|---|---|---|---|
| 3-Ph—Ph—1O—Ph5—O2 general formula (I) |  | 3 |  |  |
| 3-Ph—Ph1—1O—Ph5—O2 general formula (I) |  |  | 3 |  |
| 3-Ph—Ph5—1O—Ph5—O2 general formula (I) |  |  |  | 3 |
| 3-Cy—Ph5—O2 general formula (II-B1) | 13 | 11 | 11 | 11 |
| 5-Cy—Ph5—O2 general formula (II-B1) | 6 | 4 | 4 | 4 |
| 3-Cy—Cy—Ph5—O2 general formula (II-B3) | 10 | 13 | 13 | 13 |
| 2-Cy—Ph—Ph5—O2 general formula (II-B4) | 5 | 4 | 4 | 4 |
| 3-Cy—Ph—Ph5—O2 general formula (II-B4) | 10 | 8 | 8 | 8 |
| 3-Cy—Cy—V general formula (IV-1) | 32 | 33 | 33 | 33 |
| 3-Cy—Cy—V1 general formula (IV-1) | 11 | 11 | 11 | 11 |
| 3-Ph—Ph5—Ph-2 general formula (V) | 12.5 | 12.5 | 12.5 | 12.5 |
| 3-Ph—Ph—Ph1—Ph7 | 0.5 | 0.5 | 0.5 | 0.5 |
| Total | 100 | 100 | 100 | 100 |
| Tni [° C.] | 76 | 76 | 75 | 76 |
| Tcn [° C.] | −25 | −26 | −28 | −27 |
| $\Delta n$ | 0.108 | 0.108 | 0.108 | 0.108 |
| $\eta$ [mPa · s] | 14.6 | 14.5 | 14.6 | 14.7 |
| $\gamma_1$ [mPa · s] | 94 | 92 | 93 | 93 |
| $\Delta\varepsilon$ | −2.7 | −2.8 | −2.7 | −2.8 |
| $K_{33}$ [pN] | 14.0 | 14.1 | 14.1 | 14.0 |
| $\gamma_1/K_{33}$ | 6.7 | 6.5 | 6.6 | 6.6 |

Each of the liquid crystal compositions LC-9, LC-10, and LC-11 of the present invention had low viscosity ($\eta$), low rotational viscosity ($\gamma 1$), and a large elastic constant ($K_{33}$), and the value of $\gamma 1/K_{33}$ was smaller than that of LC-C of the comparative example.

The measurement results of the response speed of liquid crystal display elements including the liquid crystal compositions revealed that LC-9, LC-10, and LC-11 had sufficiently fast responses and that their response speeds were higher than LC-C by 3% or more.

Comparative Example 6 and Examples 23 to 27

Liquid crystal compositions MLC-C(Comparative example 6), MLC-9-1 (Example 23), MLC-9-2 (Example 24), MLC-9-3 (Example 25), MLC-10 (Example 26), and MLC-11 (Example 27) were prepared. Each of the liquid crystal compositions was vacuum-injected into a test cell. Then the pretilt angle was measured before and after UV irradiation. Table 6 lists the structures of the liquid crystal compositions and the measurement results of their pretilt angles.

TABLE 6

|  | Comparative example 6 MLC-C | Example 23 MLC-9-1 | Example 24 MLC-9-2 | Example 25 MLC-9-3 | Example 26 MLC-10 | Example 27 MLC-11 |
|---|---|---|---|---|---|---|
| LC-C | 99.65 |  |  |  |  |  |
| LC-9 |  | 99.65 | 99.65 | 99.65 |  |  |
| LC-10 |  |  |  |  | 99.65 |  |
| LC-11 |  |  |  |  |  | 99.65 |
| Polymerizable compound formula (M1-1) | 0.35 | 0.35 |  |  | 0.35 | 0.35 |
| Polymerizable compound formula (M1-3) |  |  | 0.35 |  |  |  |
| Polymerizable compound formula (I-33) |  |  |  | 0.35 |  |  |
| Total | 100 | 100 | 100 | 100 | 100 | 100 |
| Pretilt angle before polymerization [°] | 88.4 | 88.2 | 88.3 | 88.4 | 88.3 | 88.2 |

TABLE 6-continued

| | Comparative example 6 MLC-C | Example 23 MLC-9-1 | Example 24 MLC-9-2 | Example 25 MLC-9-3 | Example 26 MLC-10 | Example 27 MLC-11 |
|---|---|---|---|---|---|---|
| Pretilt angle before polymerization [°] | 86.8 | 86.7 | 86.9 | 85.2 | 86.8 | 86.6 |

As with MLC-C, the UV irradiation imparted appropriate pretilt angles to the liquid crystal compositions MLC-9-1, MLC-9-2, MLC-9-3, MLC-10, and MLC-11 of the present invention. The measurement results of response speeds of liquid crystal display elements including the liquid crystal compositions revealed that MLC-9-1, MLC-9-2, MLC-9-3, MLC-10, and MLC-11 had sufficiently fast responses and that their response speeds were higher than MLC-B by 3% or more.

The results demonstrated that each of the liquid crystal compositions of the present invention had sufficiently low viscosity ($\eta$), sufficiently low rotational viscosity ($\gamma 1$), a large elastic constant ($K_{33}$), and a negative dielectric anisotropy ($\Delta\varepsilon$) whose absolute value was large, without reducing the refractive index anisotropy ($\Delta n$) or the nematic-isotropic liquid phase transition temperature ($T_{ni}$) and that thus, for example, the VA-, PSA-, and PSVA-mode liquid crystal display elements including the liquid crystal compositions had excellent display quality and high response speeds.

The invention claimed is:

1. A nematic liquid crystal composition comprising at least one compound represented by general formula (I):

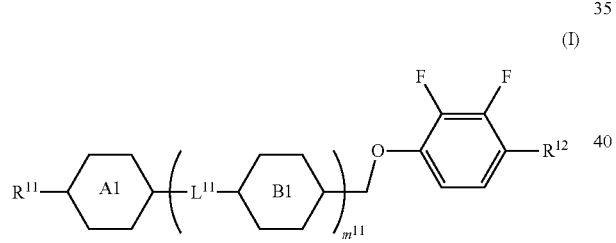

(I)

wherein in the formula, $R^{11}$ and $R^{12}$ each represent an alkyl group having 1 to 8 carbon atoms or an alkenyl group having 2 to 8 carbon atoms, —CH$_2$— or nonadjacent two or more —CH$_2$—'s in the group may be independently replaced with —O— or —S—, one or two or more hydrogen atoms present in the group may be independently replaced with a fluorine atom or a chlorine atom,
$L^{11}$ represents a single bond,
$m^{11}$ represents 1,
ring A1 represents a 1,4-phenylene group, ring B1 independently represents a 1,4-phenylene group,
and at least one compound selected from the group consisting of compounds represented by general formulae (IV-1) to (IV-3):

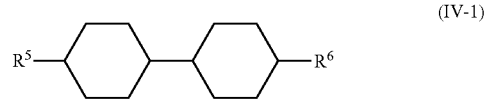

(IV-1)

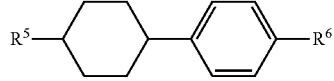

(IV-2)

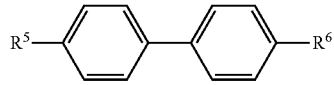

(IV-3)

wherein in each of the formulae, $R^5$ represents an alkyl group having 1 to 5 carbon atoms or an alkenyl group having 2 to 5 carbon atoms, $R^6$ represents an alkyl group having 1 to 5 carbon atoms, an alkoxyl group having 1 to 5 carbon atoms, an alkenyl group having 2 to 5 carbon atoms, or an alkenyloxy group having 2 to 5 carbon atoms and wherein the content of compounds represented by general formula (I) is at least 3% by mass.

2. The nematic liquid crystal composition according to claim 1, further comprising one or two or more compounds represented by general formula (N3):

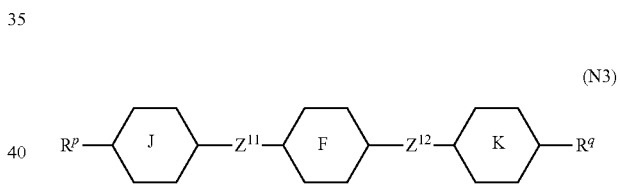

(N3)

wherein in the formula, $R^p$ and $R^q$ each independently represent an alkyl group having 1 to 10 carbon atoms or an alkenyl group having 2 to 10 carbon atoms; —CH$_2$— or two or more nonadjacent —CH$_2$—'s present in the group may be independently replaced with —O— or —S—; one or two or more hydrogen atoms present in the group may be replaced with a fluorine atom or a chlorine atom; ring J, ring F, and ring K each independently represent a trans-1,4-cyclohexylene group, a 1,4-phenylene group, a 2-fluoro-1,4-phenylene group, a 3-fluoro-1,4-phenylene group, a 3,5-difluoro-1,4-phenylene group, a 1,4-cyclohexenylene group, a 1,4-bicyclo[2.2.2]octylene group, a piperidine-1,4-diyl group, a naphthalene-2,6-diyl group, a decahydronaphthalene-2,6-diyl group, or a 1,2,3,4-tetrahydronaphthalene-2,6-diyl group; $Z^{11}$ and $Z^{12}$ each independently represent —OCH$_2$—, —CH$_2$O—, —CF$_2$O—, —OCF$_2$—, —CH$_2$CH$_2$—, —CF$_2$CF$_2$—, or a single bond; and when a plurality of $Z^{11}$'s and a plurality of $Z^{12}$'s are present, they may be the same or different.

3. The nematic liquid crystal composition according to claim 1, further comprising one or two or more compounds represented by general formula (II):

(II)

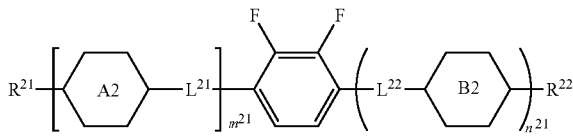

wherein in the formula, $R^{21}$ and $R^{22}$ each represent an alkyl group having 1 to 8 carbon atoms or an alkenyl group having 2 to 8 carbon atoms, —CH$_2$— or nonadjacent two or more —CH$_2$—'s in the group may be independently replaced with —O— or —S—, one or two or more hydrogen atoms present in the group may be independently replaced with a fluorine atom or a chlorine atom, $L^{21}$ and $L^{22}$ each represent —OCH$_2$—, —CH$_2$O—, —CF$_2$O—, —OCF$_2$—, —CH$_2$CH$_2$—, —CF$_2$CF$_2$—, or a single bond, when a plurality of $L^{11}$'s and a plurality of $L^{22}$'s are present, they may be the same or different, $m^{21}$ and $n^{21}$ each independently represent 0, 1, or 2, $m^{21}+m^{m2}$ represents 1, 2, or 3, Ring A2 and ring B2 each independently represent a trans-1,4-cyclohexylene group, a 1,4-phenylene group, a 2-fluoro-1,4-phenylene group, a 3-fluoro-1,4-phenylene group, a 3,5-difluoro-1,4-phenylene group, a 2,3-difluoro-1,4-phenylene group, a 1,4-cyclohexenylene group, a 1,4-bicyclo [2.2.2]octylene group, a piperidine-1,4-diyl group, a naphthalene-2,6-diyl group, a decahydronaphthalene-2,6-diyl group, or a 1,2,3,4-tetrahydronaphthalene-2,6-diyl group, when a plurality of rings A2 and/or a plurality of rings B2 are present, they may be the same or different, and ring A2 and ring B2 may be each independently substituted with an alkyl group having 1 to 12 carbon atoms, a halogenated alkyl group having 1 to 12 carbon atoms, an alkoxy group having 1 to 12 carbon atoms, a halogenated alkoxy group having 1 to 12 carbon atoms, a halogen, a cyano group, or a nitro group, provided that none of the compounds represented by formula (I) are included.

4. The nematic liquid crystal composition according to claim 3, wherein the compound represented by general formula (II) comprises one or two or more compounds represented by general formula (V):

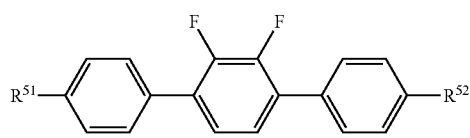

wherein in the formula, $R^{51}$ and $R^{52}$ each independently represent an alkyl group having 1 to 8 carbon atoms or an alkenyl group having 2 to 8 carbon atoms, one —CH$_2$— or two or more nonadjacent —CH$_2$—'s present in the group may be independently replaced with —O— or —S—, and one or two or more hydrogen atoms present in the group may be replaced with a fluorine atom.

5. The nematic liquid crystal composition according to claim 1, further comprising one or two or more compounds selected from the group consisting of compounds represented by general formulae (Np-1) and (Np-2):

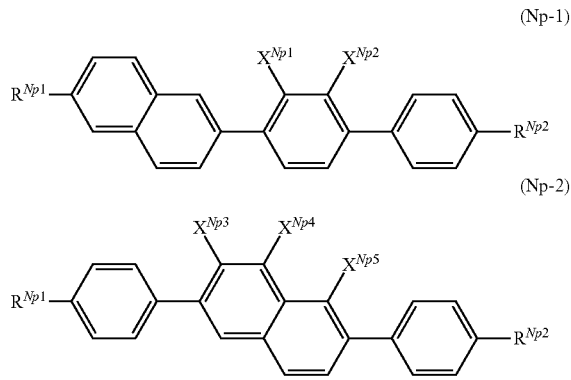

wherein in each of the formulae, $R^{Np1}$ and $R^{Np2}$ each independently represent an alkyl group having 1 to 5 carbon atoms or an alkenyl group having 2 to 5 carbon atoms, one —CH$_2$— or two or more nonadjacent —CH$_2$—'s present in the group may be independently replaced with —O— or —S—, one or two or more hydrogen atoms present in the group may be independently replaced with a fluorine atom, and $X^{Np1}$, $X^{Np2}$, $X^{Np3}$, $X^{Np4}$, and $X^{Np5}$ each independently represent a hydrogen atom or a fluorine atom.

6. The nematic liquid crystal composition according to claim 1, wherein the liquid crystal composition has a dielectric anisotropy ($\Delta\varepsilon$) of -2.0 to -8.0 at 25° C., a refractive index anisotropy ($\Delta$n) of 0.08 to 0.14 at 20° C., a viscosity ($\eta$) of 5 to 30 mPa·s at 20° C., a rotational viscosity ($\gamma$1) of 50 to 150 mPa·s at 20° C., and a nematic-isotropic liquid phase transition temperature ($T_{ni}$) of 60° C. to 120° C.

7. The nematic liquid crystal composition according to claim 1, further comprising one or two or more polymerizable compounds.

8. The nematic liquid crystal composition according to claim 7, wherein the polymerizable compound is a compound represented by general formula (RM-1):

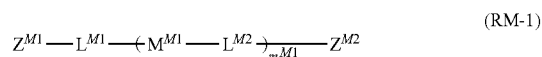
(RM-1)

wherein in the formula, $Z^{M1}$ and $Z^{M2}$ each independently represent

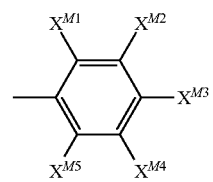

wherein $X^{M1}$ to $X^{M5}$ each represent hydrogen, fluorine, or

—$S^{M1}$—$R^{M1}$, at least one of $X^{M1}$ to $X^{M5}$ represents

—$S^{M1}$—$R^{M1}$ wherein $S^{M1}$ represents an alkylene group having 1 to 12 carbon atoms or a single bond, —CH₂— in the alkylene group may be replaced with an oxygen atom, —COO—, —OCO—, or —OCOO—, provided that oxygen atoms are not directly bonded together, $R^{M1}$ represents one of formulae (R-1) to (R-15):

(R-1) 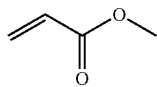

(R-2) 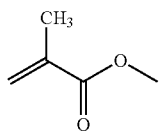

(R-3) 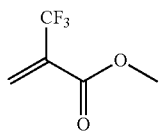

(R-4) 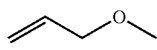

(R-5) 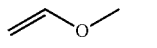

(R-6) 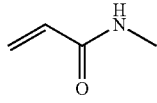

(R-7) 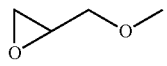

(R-8) 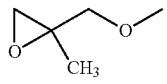

(R-9) 

(R-10) 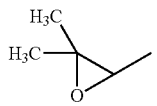

(R-11) 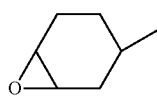

(R-12) 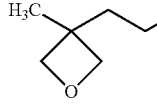

(R-13) 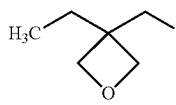

(R-14) 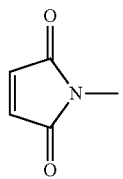

(R-15) HS—

$L^{M1}$ and $L^{M2}$ each independently represent a single bond, —O—, —CH₂—, —OCH₂—, —CH₂O—, —CO—, —C₂H₄—, —COO—, —OCO—, —CH=CH—COO—, —COO—CH=CH—, —OCO—CH=CH—, —CH=CH—OCO—, —COOC₂H₄—, —OCOC₂H₄—, —C₂H₄OCO—, —C₂H₄COO—, —OCOCH₂—, —CH₂COO—, —CH=CH—, —CF=CH—, —CH=CF—, —CF=CF—, —CF₂—, —CF₂O—, —OCF₂—, —CF₂CH₂—, —CH₂CF₂—, —CF₂CF₂—, or —C≡C—, when a plurality of $L^{M2}$'s are present, they may be the same or different, $M^{M1}$ present represents a 1,4-phenylene group, a 1,4-cyclohexylene group, or a naphthalene-2,6-diyl group, a hydrogen atom in the group may be replaced with a fluorine atom, a chlorine atom, an alkyl group having 1 to 8 carbon atoms, a halogenated alkyl group, a halogenated alkoxy group, an alkoxy group, a nitro group, or

—$S^{M1}$—$R^{M1}$ $m^{M1}$ represents 0, 1, or 2, and when $X^{M1}$ to $X^{M5}$, $S^{M1}$, $R^{M1}$, $L^{M2}$, and/or $M^{M1}$ is present in a plurality, they may be the same or different.

9. A liquid crystal display element comprising the nematic liquid crystal composition according to claim 1.

10. An active matrix-addressed liquid-crystal display element comprising the nematic liquid crystal composition according to claim 1.

11. A VA-, PSA-, PSVA-, IPS-, or ECB-mode liquid crystal display element comprising the nematic liquid crystal composition according to claim 1.

12. The nematic liquid crystal composition according to claim 1, further comprising at least one compound according to the general formula (I):

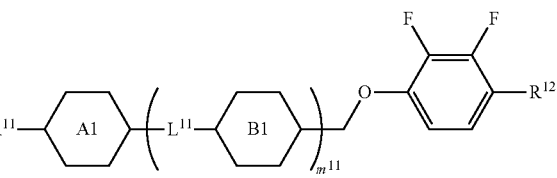

(I)

wherein in the formula, $R^{11}$ and $R^{12}$ each represent an alkyl group having 1 to 8 carbon atoms or an alkenyl group having 2 to 8 carbon atoms, —CH₂— or non-adjacent two or more —CH₂—'s in the group may be independently replaced with —O— or —S—, one or two or more hydrogen atoms present in the group may be independently replaced with a fluorine atom or a chlorine atom, wherein in the formula, $R^{11}$ and $R^{12}$ each represent an alkyl group having 1 to 8 carbon atoms or an alkenyl group having 2 to 8 carbon atoms, —$CH_2$— or non-adjacent two or more —$CH_2$—'s in the group may be independently replaced with —O— or —S—, one or two or more hydrogen atoms present in the group may be independently replaced with a fluorine atom or a chlorine atom, $L^{11}$ represents —$OCH_2$—, —$CH_2O$—, —$CF_2O$—, —$OCF_2$—, —$CH_2CH_2$—, —$CF_2CF_2$—, or a single bond, when a plurality of $L^{11}$'s are present, they may be the same or different, $m^{11}$ represents 0, 1, or 2, ring A1 represents a 1,4-phenylene group, ring B1 independently represents a trans-1,4-cyclohexylene group, a 1,4-phenylene group, a 2-fluoro-1,4-phenylene group, a 3-fluoro-1,4-phenylene group, a 3,5-difluoro-1,4-phenylene group, a 2,3-difluoro-1,4-phenylene group, a 1,4-cyclohexenylene group, a 1,4-bicyclo[2.2.2]octylene group, a piperidine-1,4-diyl group, a naphthalene-2,6-diyl, a decahydronaphthalene-2,6-diyl group, or a 1,2,3,4-tetrahydronaphthalene-2,6-diyl group, when a plurality of rings B1 are present, they may be the same or different, and ring B1 may be substituted with an alkyl group having 1 to 12 carbon atoms, a halogenated alkyl group having 1 to 12 carbon atoms, an alkoxy group having 1 to 12 carbon atoms, a halogenated alkoxy group having 1 to 12 carbon atoms, a halogen, a cyano group, or a nitro group, and excluding a compound wherein when $L^{11}$ represents a single bond, $m^{11}$ represents 1, ring A1 represents a 1,4-phenylene group, and ring B1 represents a 1,4-phenylene group.

13. The nematic liquid crystal composition according to claim 12, wherein the content of compounds represented by general formula (I) is 3% to 50% by mass.

\* \* \* \* \*